US011512339B2

(12) United States Patent
George et al.

(10) Patent No.: US 11,512,339 B2
(45) Date of Patent: Nov. 29, 2022

(54) ARRAYS INCLUDING A RESIN FILM AND A PATTERNED POLYMER LAYER

(71) Applicants: ILLUMINA, INC., San Diego, CA (US); ILLUMINA CAMBRIDGE LIMITED, Cambridge (GB)

(72) Inventors: Wayne N. George, Ilford (GB); Alexandre Richez, Cambourne (GB); M. Shane Bowen, Encinitas, CA (US); Andrew A. Brown, Cambridge (GB); Dajun Yuan, San Diego, CA (US); Audrey Rose Zak, Carlsbad, CA (US); Sean M. Ramirez, San Diego, CA (US); Raymond Campos, Santee, CA (US)

(73) Assignees: Illumina, Inc., San Diego, CA (US); Illumina Cambridge Limited, Cambridge (GB)

(*) Notice: Subject to any disclaimer, the term of this patent is extended or adjusted under 35 U.S.C. 154(b) by 1199 days.

(21) Appl. No.: 15/848,640

(22) Filed: Dec. 20, 2017

(65) Prior Publication Data

US 2018/0179575 A1 Jun. 28, 2018

Related U.S. Application Data

(60) Provisional application No. 62/438,024, filed on Dec. 22, 2016.

(51) Int. Cl.
*C09D 183/06* (2006.01)
*C12Q 1/68* (2018.01)
*C09D 133/26* (2006.01)
*C08G 77/14* (2006.01)

(52) U.S. Cl.
CPC ............. *C12Q 1/68* (2013.01); *C09D 133/26* (2013.01); *C09D 183/06* (2013.01); *C08G 77/14* (2013.01)

(58) Field of Classification Search
None
See application file for complete search history.

(56) References Cited

U.S. PATENT DOCUMENTS

| 5,767,206 | A  | 6/1998  | Ariagno et al. |
| 5,770,721 | A  | 6/1998  | Ershov et al.  |
| 7,057,026 | B2 | 6/2006  | Barnes et al.  |
| 7,211,414 | B2 | 5/2007  | Hardin et al.  |
| 7,315,019 | B2 | 1/2008  | Turner et al.  |
| 7,329,492 | B2 | 2/2008  | Hardin et al.  |
| 7,405,281 | B2 | 7/2008  | Xu et al.      |
| 8,293,354 | B2 | 10/2012 | Fu et al.      |
| 8,597,630 | B2 | 12/2013 | Song et al.    |
| 8,778,848 | B2 | 7/2014  | Lin et al.     |
| 8,778,849 | B2 | 7/2014  | Bowen et al.   |
| 8,795,782 | B2 | 8/2014  | Meagher et al. |
| 9,012,022 | B2 | 4/2015  | George et al.  |
| 9,079,148 | B2 | 7/2015  | Rigatti et al. |
| 2004/0202622 | A1 | 10/2004 | Quadir        |
| 2005/0136538 | A1 | 6/2005  | Pathak et al. |
| 2008/0108082 | A1 | 5/2008  | Rank et al.   |
| 2009/0068586 | A1 | 3/2009  | Nakamura et al. |
| 2011/0059865 | A1 | 3/2011  | Smith et al.  |
| 2013/0116153 | A1 | 5/2013  | Bowen et al.  |
| 2013/0341736 | A1 | 12/2013 | Kohl et al.   |
| 2014/0010970 | A1 | 1/2014  | Lee           |
| 2014/0017457 | A1 | 1/2014  | Megaridis et al. |
| 2014/0079923 | A1 | 3/2014  | George et al. |
| 2014/0243224 | A1 | 8/2014  | Barnard et al. |
| 2015/0005447 | A1 | 1/2015  | Berti et al.  |
| 2015/0376443 | A1 | 12/2015 | Chou et al.   |
| 2016/0122816 | A1 | 5/2016  | Brown et al.  |
| 2016/0199832 | A1 | 7/2016  | Jamshidi et al. |
| 2016/0246170 | A1 | 8/2016  | Bowen et al.  |

FOREIGN PATENT DOCUMENTS

| CN | 101805519 A | 8/2010 |
| CN | 102015524 A | 4/2011 |
| CN | 103146146 B | 6/2015 |
| CN | 105431554 A | 3/2016 |
| CN | 105785712 A | 7/2016 |
| CN | 105916689 A | 8/2016 |
| EP | 1730773 B1 | 9/2008 |
| EP | 2566311 A1 | 3/2013 |
| JP | 2004189840 A | 7/2004 |
| JP | 2015501734 A | 1/2015 |
| JP | 2016108445 A | 6/2016 |
| KR | 1020160081896 A1 | 7/2016 |
| RU | 2041261 C1 | 8/1995 |
| WO | WO 91/06678 | 5/1991 |
| WO | WO 2000/031148 | 6/2000 |

(Continued)

OTHER PUBLICATIONS

Bentley et al., "Accurate whole human genome sequencing using reversible terminator chemistry", Nature, 2008, 456:53-59, Macmillan Publishers Limited.

(Continued)

*Primary Examiner* — Christopher M Gross
(74) *Attorney, Agent, or Firm* — Illumina, Inc.

(57) ABSTRACT

An example of an array includes a support, a cross-linked epoxy polyhedral oligomeric silsesquioxane (POSS) resin film on a surface of the support, and a patterned hydrophobic polymer layer on the cross-linked epoxy POSS resin film. The patterned hydrophobic polymer layer defines exposed discrete areas of the cross-linked epoxy POSS resin film, and a polymer coating is attached to the exposed discrete areas. Another example of an array includes a support, a modified epoxy POSS resin film on a surface of the support, and a patterned hydrophobic polymer layer on the modified epoxy POSS resin film. The modified epoxy POSS resin film includes a polymer growth initiation site, and the patterned hydrophobic polymer layer defines exposed discrete areas of the modified epoxy POSS resin film. A polymer brush is attached to the polymer growth initiation site in the exposed discrete areas.

13 Claims, 3 Drawing Sheets

(56) References Cited

FOREIGN PATENT DOCUMENTS

| WO | WO 2001/001143 | 1/2001 |
|----|----------------|--------|
| WO | WO 2003/0014392 | 2/2003 |
| WO | WO 04/018497 | 3/2004 |
| WO | WO 07/123744 | 11/2007 |
| WO | WO2011/011140 A2 | 1/2011 |
| WO | 2011/059967 A2 | 5/2011 |
| WO | 2013/086083 A1 | 6/2013 |
| WO | 2015/031849 A1 | 3/2015 |
| WO | 2015/095291 A1 | 6/2015 |
| WO | 2015/200421 A1 | 12/2015 |
| WO | 2016/066586 A1 | 5/2016 |

OTHER PUBLICATIONS

International Search Report and Written Opinion for International Application No. PCT/US2017/067557 dated Apr. 27, 2018, 24 pages.
Ro, et al., "Silsesquioxanes in nanoscale patterning applications," Materials Today, Jan.-Feb. 2011, vol. 14, No. 1-2.

ROUTE A | ROUTE B TO FORM 14'

TO FIG. 1C

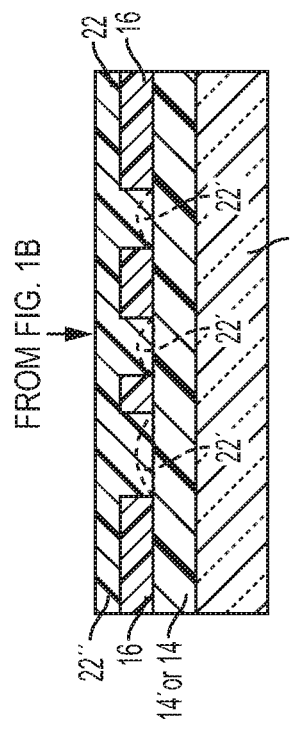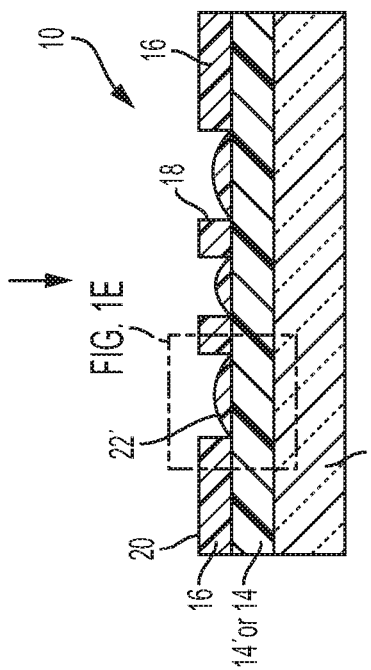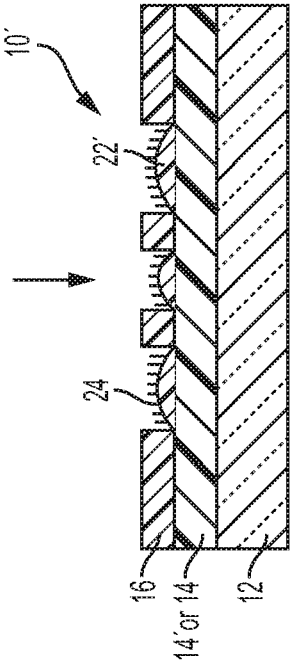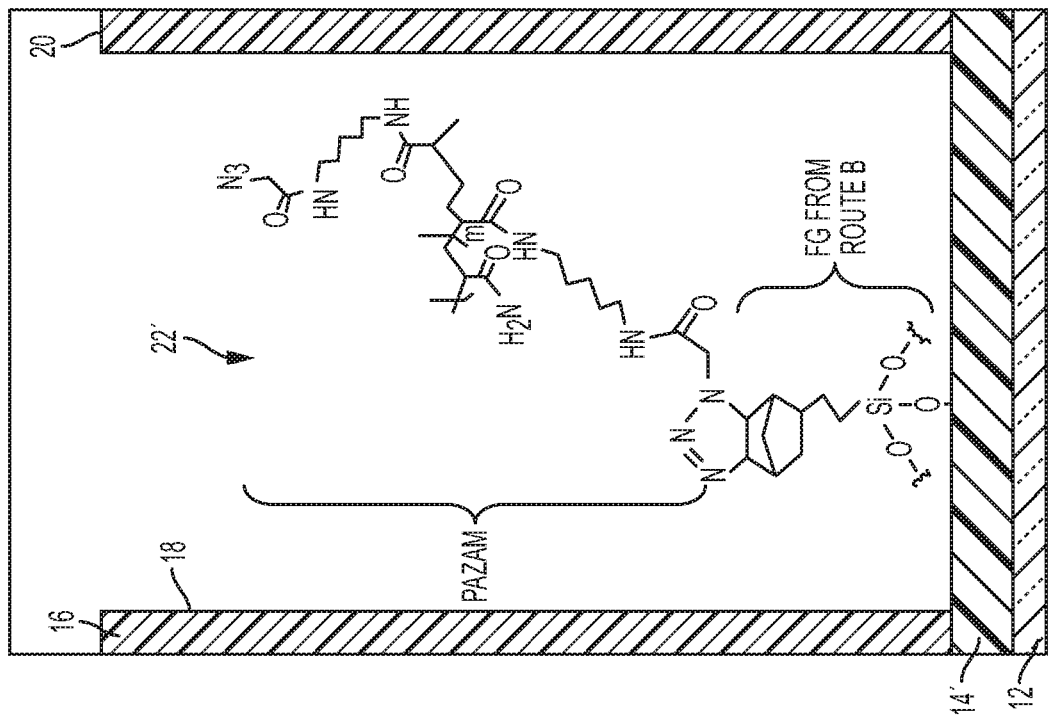

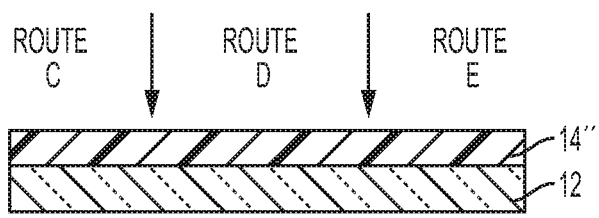
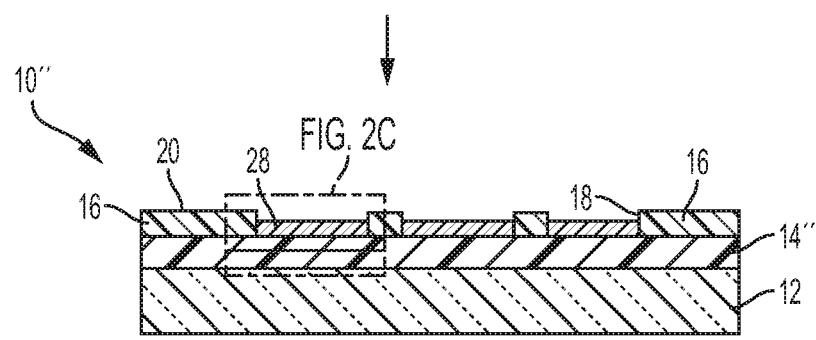
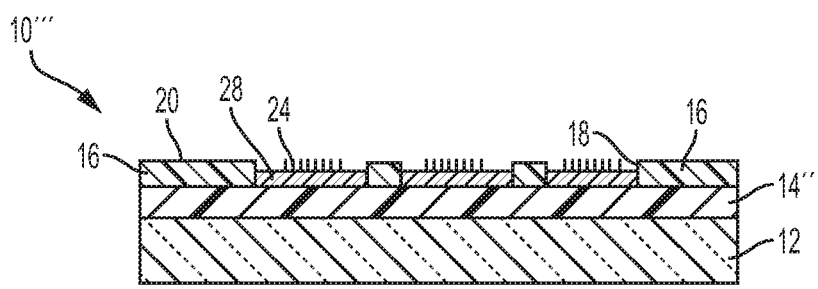
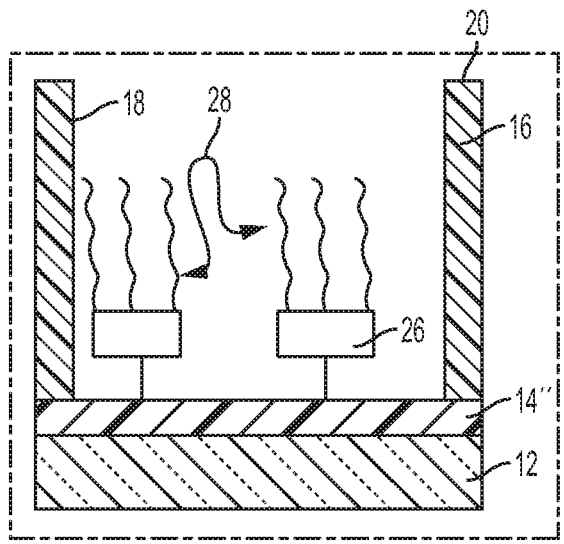

ARRAYS INCLUDING A RESIN FILM AND A PATTERNED POLYMER LAYER

CROSS-REFERENCE TO RELATED APPLICATIONS

This application claims the benefit of U.S. Provisional Application Ser. No. 62/438,024, filed Dec. 22, 2016, the contents of which is incorporated by reference herein in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes in humans and other organisms. In certain applications, for example, individual DNA and RNA probes may be attached at small locations in a geometric grid (or randomly) on an array support. A test sample, e.g., from a known person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

SUMMARY

In some aspects is a composition comprising a support and a cross-linked epoxy POSS resin film on a surface of the support. In some aspects the composition is suitable as an array for oligonucleotide sequencing or as a production intermediate. In some aspects, the resin film is patterned to define discrete areas within interstitial regions, and in some aspects, the discrete areas are wells. In other aspects, the composition comprises a hydrophobic polymer layer on the patterned resin film, including the discrete areas defined by the pattern (e.g., in the wells) and the interstitial regions. In other aspects, the hydrophobic polymer layer is patterned to expose the resin film in the discrete areas or wells while remaining on the resin film in the interstitial areas of the resin film between the discrete areas or wells. In still other aspects, a polymer coating is attached to the patterned resin film in the exposed discrete areas of the cross-linked epoxy POSS resin film. The composition may further comprise an amplification primer grafted to the polymer coating. The cross-linked POSS resin film optionally comprises a polymer growth initiation site as described herein. In still other aspects, a polymer brush is attached to the polymer growth initiation site in the exposed discrete areas of the cross-linked epoxy POSS resin film.

In some aspects are methods of making the composition comprising a support and a cross-linked epoxy POSS resin film on a surface of the support, comprising forming the cross-linked epoxy POSS resin film on a support surface, where the forming involves mixing a support-bound epoxy silane with one or more epoxy-functionalized POSS reagents in the presence of a photoacid generator and optionally a sensitizer to form a support-bound resin precursor, and curing the resin precursor to form a support-bound cross-linked epoxy POSS resin film. Such methods may further comprise reacting a surface of a support with an epoxy silane to form the support-bound epoxy silane. In some aspects, the resin film is patterned to define discrete areas within interstitial regions, and in some aspects, the discrete areas are wells. Such methods may further comprise forming a hydrophobic polymer layer on the cross-linked, support-bound epoxy POSS resin film on the support surface, wherein the hydrophobic polymer layer is patterned to expose the resin film in the discrete areas or wells while remaining on the resin film in the interstitial areas of the resin film between the discrete areas or wells.

In a first aspect is an array that includes a support, a cross-linked epoxy polyhedral oligomeric silsesquioxane (POSS) resin film on a surface of the support, and a patterned hydrophobic polymer layer on the cross-linked epoxy POSS resin film, wherein the patterned hydrophobic polymer layer defines exposed discrete areas of the cross-linked epoxy POSS resin film, and a polymer coating is attached to the exposed discrete areas.

In some aspects are methods of forming arrays of this first aspect, which comprise forming a patterned hydrophobic polymer layer on a cross-linked epoxy POSS resin film on a support surface, thereby exposing discrete areas of the cross-linked epoxy POSS resin film. This method may further comprise applying a polymer coating to form an attached coating portion on the exposed discrete areas and an unattached coating portion on the patterned hydrophobic layer; and washing the unattached coating portion off of the patterned hydrophobic layer. The method may further comprise forming the cross-linked epoxy POSS resin film on the support surface, the forming involving: mixing an epoxy silane and at least one epoxy POSS monomeric unit in the presence of a photoacid generator and optionally a sensitizer to form a resin precursor; depositing the resin precursor on the support surface; and curing the resin precursor to form the cross-linked epoxy POSS resin film.

In a second aspect, an array includes a support, a modified epoxy POSS resin film on a surface of the support, and a patterned hydrophobic polymer layer on the modified epoxy POSS resin film, where the patterned hydrophobic polymer layer defines exposed discrete areas of the cross-linked epoxy POSS resin film. In some instances, the modified epoxy POSS resin film includes a polymer growth initiation site, and the patterned hydrophobic polymer layer defines exposed discrete areas of the modified epoxy POSS resin film. A polymer brush is attached to the polymer growth initiation site in the exposed discrete areas. In some respects, the array comprises a support, a modified epoxy polyhedral oligomeric silsesquioxane (POSS) resin film on a surface of the support, the modified epoxy POSS resin film including a polymer growth initiation site, a patterned hydrophobic polymer layer on the modified epoxy POSS resin film, the patterned hydrophobic polymer layer defining exposed discrete areas of the modified epoxy POSS resin film, and a polymer brush attached to the polymer growth initiation site in the exposed discrete areas.

Methods for producing arrays of the second aspect as described herein comprise forming a patterned hydrophobic polymer layer on a modified epoxy polyhedral oligomeric silsesquioxane (POSS) resin film on a support surface, thereby exposing discrete areas of the modified epoxy POSS resin film. The modified epoxy POSS resin film includes a polymer growth initiation site. In some aspects, a polymer brush is grown from the polymer growth initiation site in the exposed discrete areas. Thus, in some aspects, a second aspect of the method disclosed herein comprises forming a patterned hydrophobic polymer layer on a modified epoxy polyhedral oligomeric silsesquioxane (POSS) resin film on a support surface, thereby exposing discrete areas of the modified epoxy POSS resin film, wherein the modified epoxy POSS resin film includes a polymer growth initiation site; and growing a polymer brush from the polymer growth initiation site in the exposed discrete areas. In some aspects, the method further comprises forming the modified epoxy POSS resin film, where the forming involves mixing an epoxy silane, at least one epoxy POSS monomeric unit, and an epoxy-functionalized polymerization agent (e.g., a radical polymerization agent, a cationic polymerization agent, an anionic polymerization agent, a ring-opening methathesis polymerization agent, or a controlled radical polymerization agent) or controlled radical polymerization (CRP) agent in the presence of a photoacid generator and an optional sensitizer to form a resin precursor; depositing the resin precursor on the support surface; and curing the resin precursor to form the modified epoxy POSS resin film. In some aspects, the at least one epoxy POSS monomeric unit is epoxycyclohexylalkyl POSS and glycidyl POSS.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 1A through 1F are cross-sectional views illustrating an example of the method disclosed herein, where FIG. 1E is an enlarged view of a depression of the array that is formed; and FIGS. 2A through 2D are cross-sectional views illustrating another example of the method disclosed herein, where FIG. 2C is an enlarged view of a depression of the array that is formed.

DETAILED DESCRIPTION

Figure 1A:
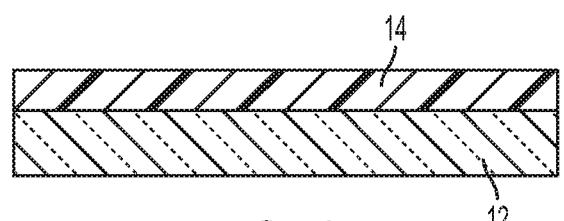

It is to be understood that any features of the first aspect of the array may be combined together in any desirable manner. Moreover, it is to be understood that any combination of features of the first aspect and/or first method may be used together, and/or that any features from either or both of these aspects may be combined with any of the examples disclosed herein.

In some instances of the methods, compositions, and arrays described herein, the cross-linked epoxy POSS resin film is patterned to define features such as wells and intervening interstitial regions between the features, and in other instances, the cross-linked epoxy POSS resin film is not patterned. In instances in which the cross-linked epoxy POSS resin film is patterned, the pattern in the film defines features that are the discrete portions that are also exposed by the pattern of the patterned hydrophobic layer, e.g., the resin film comprises wells, and the discrete regions exposed by the patterned hydrophobic layer are the wells in the film.

Examples of the method disclosed herein use the different epoxy POSS resin films in combination with the patterned hydrophobic layer to confine where a polymer is applied or grows, or to allow for preferential removal of the polymer from regions with the patterned hydrophobic layer over regions with exposed resin film. These methods eliminate the need for mechanical or chemical polymer removal processes, such as polishing, that are performed when the polymer is blanketly deposited across the entire resin or solid support surface.

In one example of the method disclosed herein, a cross-linked epoxy polyhedral oligomeric silsesquioxane (POSS) resin film is used in combination with a patterned hydrophobic layer. The patterned hydrophobic layer exposes discrete portions of the cross-linked epoxy POSS resin film, which serve as capture pads for a subsequently applied polymeric material, in part because the polymeric material is more hydrophilic than the patterned hydrophobic layer. The surface energy of the polymeric material is closer to the surface energy of the cross-linked epoxy POSS resin film than to the surface energy of the patterned hydrophobic layer, and thus the polymeric material has better wetting onto the cross-linked epoxy POSS resin film. In some instances, the resin film is chemically modified with capture groups that are capable of forming covalent bonds with functional groups on the polymeric material.

An example of this first aspect of the method further comprises forming the cross-linked epoxy POSS resin film on the support surface, where the forming involves mixing an epoxy silane, epoxycyclohexylalkyl POSS, and glycidyl POSS in the presence of a photoacid generator and optionally a sensitizer to form a resin precursor; depositing the resin precursor on the support surface; and curing the resin precursor to form the cross-linked epoxy POSS resin film.

In this first aspect of the method, prior to forming the patterned hydrophobic polymer layer, the method can further comprise exposing the cross-linked epoxy POSS resin film to plasma aching or a chemical treatment to introduce —OH groups such as hydroxyl (C—OH or Si—OH) groups and/or carboxyl groups to the cross-linked epoxy POSS resin film. In some aspects, the method further comprises attaching functional groups to at least some of the —OH groups, the functional groups being selected from the group consisting of:

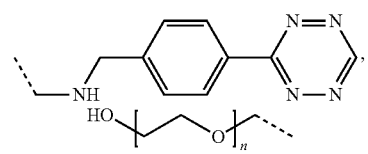

wherein n ranges from 1 to 20,

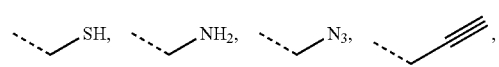

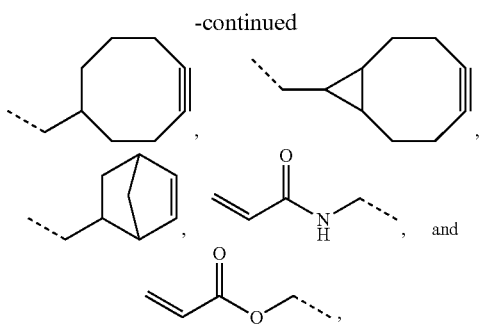

and wherein - - - represents an alkylsilane (e.g., by reaction of the hydroxyl groups with a trialkoxyalkylsilane), a poly(ethylene glycol)-silane (e.g., by reaction of the hydroxyl groups with a trialkoxysilane poly(ethylene glycol)), an alkyl (e.g., by reaction of the hydroxyl groups with an alkyl halide), or a polyethylene glycol chain.

Another example of this first aspect of the method further comprises forming the cross-linked epoxy POSS resin film on the support surface, where the forming involves mixing, in the presence of an optional sensitizer and a photoacid generator, an epoxy silane, epoxycyclohexylalkyl POSS, glycidyl POSS, and a POSS core including at least one epoxy functional group and a non-epoxy functional group to form a resin precursor; depositing the resin precursor on the support surface; and curing the resin precursor to form the cross-linked epoxy POSS resin film.

In another example of this first aspect, the method comprises forming the cross-linked epoxy POSS resin film on the support surface, where the forming involves mixing, in the presence of a photoacid generator and optionally a sensitizer, a support-bound epoxy silane with one or more epoxy-functionalized POSS reagents and a POSS core including one epoxy functional group and a non-epoxy functional group to form a support-bound resin precursor, and curing the resin precursor to form a support-bound cross-linked epoxy POSS resin film.

In an example of this first aspect of the method, washing involves sonication in water. In another example, washing involves dunk washing and spraying or mechanical scrubbing.

In an example of this first aspect of the method, forming the patterned hydrophobic polymer layer involves i) depositing a hydrophobic polymer on the cross-linked epoxy POSS resin film and patterning the deposited hydrophobic polymer using at least one of nanoimprint lithography and photolithography; or ii) depositing the hydrophobic polymer in a pattern on the cross-linked epoxy POSS resin film using patterned printing, for example, at least one of inkjet printing and microcontact printing, or aerosol patterned printing.

In examples of this first aspect of the method further comprises grafting an amplification primer to the attached coating portion. Examples of the first aspect of the array further comprise amplification primers grafted to the attached coating portion.

In these first aspects of the method and array, the patterned hydrophobic layer is selected from the group consisting of a fluoropolymer, a negative tone photoresist, and a polysiloxane.

In another example of the method disclosed herein, a modified epoxy POSS resin film is used in combination with a patterned hydrophobic layer. The patterned hydrophobic layer exposes discrete portions of the modified epoxy POSS resin film. The modified epoxy POSS resin film includes an epoxy-functionalized controlled radical polymerization (CRP) agent, which acts as an initiator species for polymer growth. The patterned hydrophobic layer confines the polymer growth to the discrete portions.

In some examples, the polymerization agent or CRP agent is a POSS core including at least one epoxy functional group and a polymerization agent or CRP agent functional group. In some examples, the epoxy-functionalized CRP agent is an epoxy-functionalized reversible addition-fragmentation chain transfer (RAFT) agent or an epoxy-functionalized atom transfer radical polymerization (ATRP) initiator. In certain examples, a molar or mass ratio of epoxycyclohexylalkyl POSS and glycidyl POSS to epoxy-functionalized CRP agent ranges from about 1:1 to about 9:1.

Another example of this second aspect of the method comprises forming a cross-linked epoxy POSS resin film on a support surface, where the forming involves mixing a support-bound epoxy silane with one or more epoxy-functionalized POSS reagents in the presence of an epoxy-functionalized controlled radical polymerization (CRP) agent, a photoacid generator, and optionally a sensitizer, to form a support-bound resin precursor, and curing the resin precursor to form a support-bound cross-linked epoxy POSS resin film. Such examples may further comprise reacting a surface of a support with an epoxy silane to form the cross-linked, support-bound epoxy silane. Such methods may further comprise forming a patterned hydrophobic polymer layer on the cross-linked, support-bound epoxy POSS resin film on the support surface as described herein.

In this second aspect of the method, prior to forming the patterned hydrophobic polymer layer, the method can further comprise exposing the cross-linked epoxy POSS resin film to plasma ashing or a chemical treatment to introduce —OH groups (e.g., hydroxyl (C—OH, Si—OH) and/or carboxyl) groups to the cross-linked epoxy POSS resin film; and attaching functional groups or CRP agents to at least some of the hydroxyl groups, the functional groups being selected from the group consisting of:

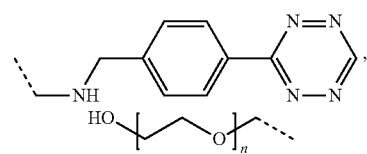

wherein n ranges from 1 to 20,

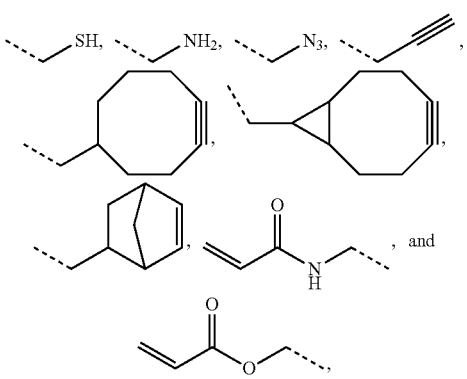

and wherein - - - represents an alkylsilane (e.g., by reaction of the hydroxyl groups with a trialkoxyalkylsilane), a poly(ethylene glycol)-silane (e.g., by reaction of the hydroxyl groups with a trialkoxysilane poly(ethylene glycol)), an alkyl (e.g., by reaction of the hydroxyl groups with an alkyl halide), or a polyethylene glycol chain.

Another example of this second aspect of the method comprises forming the modified epoxy POSS resin film, where the forming involves mixing, in the presence of an optional sensitizer and a photoacid generator, an epoxy silane, epoxycyclohexylalkyl POSS, glycidyl POSS, and a POSS core including at least one epoxy functional group and a non-epoxy functional group to form a resin precursor; depositing the resin precursor on the support surface; curing the resin precursor to form an initially modified epoxy POSS resin film; and introducing a controlled radical polymerization (CRP) agent functional group to the initially modified epoxy POSS resin film to form the modified epoxy POSS resin film. The non-epoxy functional group is (a) a reactive group that is orthogonally reactive to an epoxy group (i.e., reacts under different conditions than an epoxy group), that serves as a handle for coupling the resin to an amplification primer, a polymer, or a polymerization agent; or (b) a group that adjusts the mechanical or functional properties of the resin, e.g., surface energy adjustments. In some aspects, the non-epoxy functional group being selected from the group consisting of an azide, a thiol, a poly(ethylene glycol), a norbornene, and a tetrazine. In other aspects, the non-epoxy functional group is an amino, hydroxyl, alkynyl, ketone, aldehyde, or ester group. In other aspects, the non-epoxy functional group is an alkyl, aryl, alkoxy, or haloalkyl group.

In an example of the second aspect of the method, forming the patterned hydrophobic polymer layer involves i) depositing a hydrophobic polymer on the modified epoxy POSS resin film and patterning the deposited hydrophobic polymer using at least one of nanoimprint lithography and photolithography; or ii) depositing the hydrophobic polymer in a pattern on the modified epoxy POSS resin film using patterned printing such as at least one of inkjet printing and microcontact printing, or aerosol patterned printing.

It is to be understood that any features of the second aspect of the method may be combined together in any desirable manner. Moreover, it is to be understood that any combination of features of the first aspect of the method and/or array and/or the second aspect of the method may be used together, and/or that any features from any of these aspects may be combined with any of the examples disclosed herein.

In some examples of the second aspect of the array and method, the polymer brush is a copolymer, such as a random, ordered, or block copolymer. In some aspects, the polymer brush is further functionalized by radical exchange. Functionalization of attached polymer networks may be performed using reactive units that mediate C—H insertion reactions, such as aromatic carbonyl compounds (diphenylketone derivatives), azo compounds, sulfonyl azides, aryl azides, and aziridines.

An example of this second array further comprises an amplification primer grafted to the polymer brush. An example of this second method further comprises grafting an amplification primer to the polymer brush.

In these second aspects of the method and array, the patterned hydrophobic layer is selected from the group consisting of a fluoropolymer, a negative tone photoresist, and a polysiloxane.

It is to be understood that any features of the second aspect of the array may be combined together in any desirable manner. Moreover, it is to be understood that any combination of features of the first aspect of the method and/or array and/or the second aspect of the method and/or array may be used together, and/or that any features from any of these aspects may be combined with any of the examples disclosed herein.

In some aspects of the methods, arrays, and compositions described herein, the polymer coating includes a recurring unit of Formula (I):

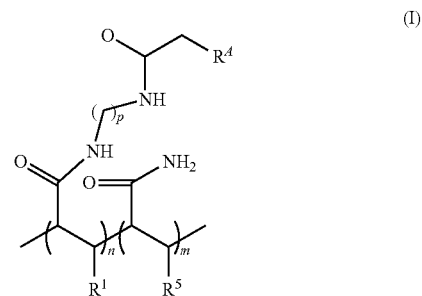

wherein:
$R^1$ is H or optionally substituted alkyl;
$R^4$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$ is selected from the group consisting of H and optionally substituted alkyl;
each of the —$(CH_2)_p$— can be optionally substituted;
p is an integer in the range of 1 to 50;
n is an integer in the range of 1 to 50,000; and
m is an integer in the range of 1 to 100,000.

In the structure of Formula (I), one of ordinary skill in the art will understand that the "n" and "m" subunits are recurring subunits that are present in a random order throughout the polymer.

A particular example of a polymer coating is poly(N-(5-azidoacetamidylpentyl) acrylamide-co-acrylamide, PAZAM (see for example, U.S. Patent Publication Nos. 2014/0079923 A1, or 2015/0005447 A1, each of which is incorporated herein by reference in its entirety), which comprises the structure shown below:

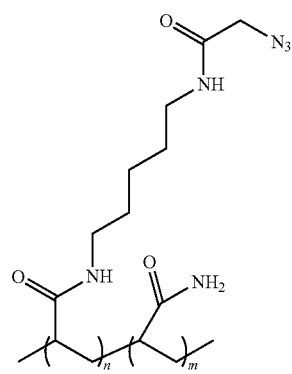

wherein n is an integer in the range of 1-20,000, and m is an integer in the range of 1-100,000. As with Formula (I), one of ordinary skill in the art will recognize that the "n" and "m" subunits are recurring units that are present in random order throughout the polymer structure.

The molecular weight of the Formula (I) or PAZAM polymer may range from about 10 kDa to about 1500 kDa, or may be, in a specific example, about 312 kDa.

In some examples, the Formula (I) or PAZAM polymer is a linear polymer. In some other examples, the Formula (I) or PAZAM polymer is a lightly cross-linked polymer. In other examples, the Formula (I) or PAZAM polymer comprises branching.

Other examples of suitable polymer materials include those having a colloidal structure, such as agarose; or a polymer mesh structure, such as gelatin; or a cross-linked polymer structure, such as polyacrylamide polymers and copolymers, silane free acrylamide (SFA, see, for example, U.S. Patent Publication No. 2011/0059865, which is incorporated herein by reference in its entirety), or an azidolyzed version of SFA. Examples of suitable polyacrylamide polymers may be formed from acrylamide and an acrylic acid or an acrylic acid containing a vinyl group as described, for example, in WO 2000/031148 (incorporated herein by reference in its entirety) or from monomers that form [2+2] photo-cycloaddition reactions, for example, as described in WO 2001/001143 or WO 2003/0014392 (each of which is incorporated herein by reference in its entirety). Other suitable polymers are co-polymers of SFA and SFA derivatized with a bromo-acetamide group (e.g., BRAPA), or co-polymers of SFA and SFA derivatized with an azido-acetamide group.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

As used herein, an "acrylate" refers to a "CH$_2$=CHCOO—" functional group (i.e.,

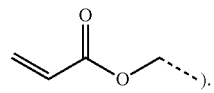

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

The alkyl may be substituted with a halide or halogen, which means any one of the radio-stable atoms of column 7 of the Periodic Table of the Elements, e.g., fluorine, chlorine, bromine, or iodine. This group is referred to as an "alkyl halide".

The alkyl may also be singular bonded to an oxygen atom. This group is an "alkoxy". An example of an alkoxy is a hydroxyl terminated ethoxy (i.e.,

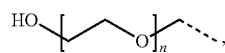

wherein n ranges from 1 to 20). This group may also be referred to as hydroxyl terminated poly(ethylene glycol).

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like. The alkenyl group may be designated as, for example, "C2-4 alkenyl," which indicates that there are two to four carbon atoms in the alkenyl chain.

As used herein, "alkynyl" refers to a straight or branched hydrocarbon chain containing one or more triple bonds (e.g.,

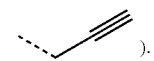

The alkynyl group may have 2 to 20 carbon atoms. The alkynyl group may be designated, for example, as "C2-4 alkynyl," which indicates that there are two to four carbon atoms in the alkynyl chain.

An "amino" functional group refers to an —NR$_a$R$_b$ group, where R$_a$ and R$_b$ are each independently selected from hydrogen (e.g.,

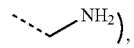

C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, which may be designated as C6-18. Examples of aryl groups include phenyl, naphthyl, azulenyl, and anthracenyl.

As used herein, the term "attached" refers to the state of two things being joined, fastened, adhered, connected or bound to each other. For example, a nucleic acid can be attached to a polymer coating by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

An "azide" or "azido" functional group refers to —N$_3$ (e.g.,

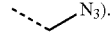

As used herein, "carbocyclyl" means a ring or ring system containing carbon atoms in the ring backbone. When the carbocyclyl is a ring system, two or more rings may be joined together in a fused, bridged or spiro-connected fashion. Carbocyclyls may have any degree of saturation, provided that at least one ring in a ring system is not aromatic.

Thus, carbocyclyls include cycloalkyls, cycloalkenyls, and cycloalkynyls. The carbocyclyl group may have 3 to 20 carbon atoms (i.e., C3-20).

As used herein, "curing" means treatment of a polymer or resin precursor to promote polymerization and cross-linking. With respect to the POSS resin film described herein, curing refers to polymerization and cross-linking of the POSS resin precursors and/or components. Curing may be accomplished under a variety of conditions, such as exposure to actinic radiation, such as visible light radiation or ultraviolet (UV) radiation, or radiation of a wavelength between about 240 and 380 nm, and/or elevated temperature. Curing radiation may be provided by an Hg lamp. Suitable curing temperatures may range from about 20° C. to about 80° C. In some instances, curing may be completed using exposure to hard bake conditions that help drive the cross-linking reaction to completion (e.g., UV initiates the polymerization/cross-linking process and the reaction continues in the dark until complete). In some instances, a hard bake also dries or dehydrates the cross-linked epoxy POSS resin film to drive out any solvent(s) that may remain after curing. Suitable hard bake temperatures include temperatures from about 100° C. to about 300° C. An example of a device that can be used for hard baking includes a hot plate.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. Examples include cyclohexenyl or cyclohexene and norbornene or norbornyl (e.g.,

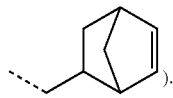

).

Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne (e.g.,

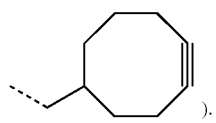

).

Another example is bicyclononyne (i.e., a bicyclic ring system, such as

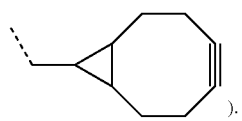

).

Also as used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, the term "carboxylic acid" or "carboxyl" as used herein refers to —C(O)OH.

The term "depositing," as used herein, refers to any suitable application technique, which may be manual or automated. Generally, depositing may be performed using vapor deposition techniques, coating techniques, grafting techniques, or the like. Some specific examples include chemical vapor deposition (CVD), plasma-enhanced CVD, initiated CVD, metal-organic CVD, spray coating, spin coating, dunk or dip coating, puddle dispensing, inkjet printing, screen printing, or microcontact printing.

As used herein, the term "depression" refers to a discrete concave feature, defined by the patterned hydrophobic layer, having a surface opening that is completely surrounded by interstitial region(s) of the patterned hydrophobic layer. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or a flow channel.

The term "each," when used in reference to a collection of items, is intended to identify an individual item in the collection, but does not necessarily refer to every item in the collection. Exceptions can occur if explicit disclosure or context clearly dictates otherwise.

The term "epoxy" as used herein refers to

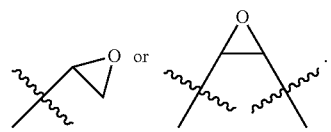

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). The heterocyclyl group may be designated as "3-6 membered heterocyclyl" or similar designations. In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

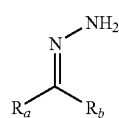

group in which $R_a$ and $R_b$ are previously defined herein.

As used herein, "hydroxyl" is an —OH group. Hydroxyl groups as described herein may be attached to carbon or silicon atoms.

As used herein, the term "interstitial region" refers to an area of the patterned hydrophobic polymer layer that separates exposed areas of an underlying resin film. An interstitial region can separate one feature that is defined by the patterned hydrophobic polymer layer (e.g., a depression) from another feature that is defined by the patterned hydrophobic polymer layer. The two features that are separated from each other can be discrete, i.e., lacking contact with each other. In another example, an interstitial region can separate a first portion of a feature from a second portion of a feature. In many examples, the interstitial region is continuous whereas the features are discrete, for example, as is the case for a plurality of wells defined in an otherwise continuous patterned hydrophobic polymer layer. The separation provided by an interstitial region can be partial or full separation. Interstitial regions have the hydrophobic polymer layer as a surface material, and the features defined by the hydrophobic polymer layer have the resin film as a surface material. The term "interstitial region" is also used herein where the resin film itself is patterned, to refer to a region that separates one feature defined by the patterned film from another feature defined by the patterned film.

An "N-amido" group refers to a "—N($R_a$)C(=O)$R_b$" group in which $R_a$ and $R_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein). An example of an N-amido group is

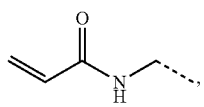

wherein $R_a$ is hydrogen and $R_b$ is a C2 alkenyl. This particular N-amido is also an acrylamide. It is to be understood that the H atom in the acrylamide could be replaced with an alkyl or another functional group, and thus a substituted acrylamide may be used. Moreover, $R_b$ could be an alkyl substituted C2 alkenyl (yielding, e.g., a methacrylamide group).

"Nitrile oxide," as used herein, means a "$R_aC\equiv N^+O^-$" group in which $R_a$ is previously defined herein. Examples of preparing nitrile oxide include in situ generation from aldoximes by treatment with chloramide-T or through action of base on imidoyl chlorides [RC(Cl)=NOH].

"Nitrone," as used herein, means a "$R_aR_bC=NR_c^+O^-$" group in which $R_a$ and $R_b$ are previously defined herein and $R_c$ is selected from C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, the term "photoacid generator" is a compound that becomes more acidic or releases proton ions upon absorption of light. Exemplary photoacid generators include iodonium salts such as bis(4-tert-butylphenyl)iodonium perfluoro-1-butanesulfonate or bis-(4-tert-butylphenyl)iodonium p-toluenesulfonate, and sulfonium triflate compounds such as (4-tert-butylphenyl)diphenylsulfonium triflate, or triphenylsulfonium triflate. In alternative embodiments, curing could be performed under thermal conditions, with reagents that release strong acid in situ upon exposure to heat.

As used herein, "plasma ashing" refers to a process of removing organic matter from a patterned wafer or surface (e.g., a resin film) by an oxygen plasma or an air plasma. The products that result from plasma ashing may be removed with a vacuum pump/system. Plasma ashing can activate a support surface by introducing reactive —OH or hydroxyl groups. Introduced hydroxyl groups can be bound to, e.g., carbon and/or silicon atoms in the resin film. Introduced groups may also include carboxyl groups.

As used herein, the terms "polymer coating" and "polymer brush" are intended to mean a semi-rigid polymeric material that is permeable to liquids and gases and that is tethered to the substrate/support. The polymer coating and polymer brush may be a hydrogel that can swell when liquid is taken up and can contract when liquid is removed by drying. The polymer coating may be deposited, and the polymer brush may be grown from a polymer growth initiation site.

As used herein, the term "polyhedral oligomeric silsesquioxane" (POSS) refers to a chemical composition that is a hybrid intermediate ($RSiO_{1.5}$) between that of silica ($SiO_2$) and silicone ($R_2SiO$). The composition is an organosilicon compound with the chemical formula $[RSiO_{3/2}]_n$, where the R groups can be the same or different. The composition may comprise one or more different cage or core structures as monomeric units. In some instances, the structure comprises a polyoctahedral cage or core structure. For example, the polyhedral structure may be a $T_8$ structure, such as:

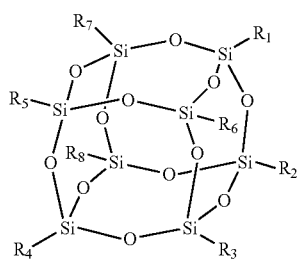

and represented by:

This monomeric unit typically has eight arms of functional groups $R_1$ through $R_8$.

The monomeric unit may have a cage structure with 10 silicon atoms and 10 R groups, referred to as $T_{10}$, such as:

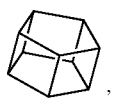, or may have a cage structure with 12 silicon atoms and 12 R groups, referred to as $T_{12}$, such as:

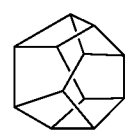.

The POSS material may comprise $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein. As examples, any of the cage structures may be present in an amount ranging from about 30% to about 100% of the total POSS monomeric units used. The POSS material may be a mixture of cage structures along with open and partially open cage structures. Thus, the POSS resin precursors and resins described herein comprise epoxy POSS materials, which may be a mixture of silsesquioxane configurations. For example, any POSS material described herein may be a mixture of discrete POSS cages and non-discrete silsesquioxane structures and/or incompletely condensed, discrete structures, such as polymers, ladders, and the like. The partially condensed materials would therefore include epoxy R groups as described herein at some silicon vertices, but some silicon atoms would not be substituted with the R groups and could be substituted instead with OH groups. In some examples, the POSS materials comprise a mixture of various forms, such as:

Condensed cages

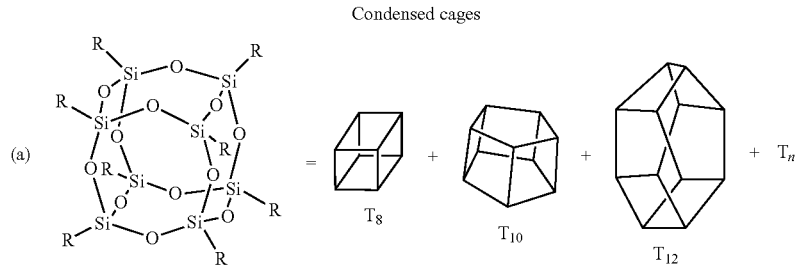

Incompletely Condensed cages

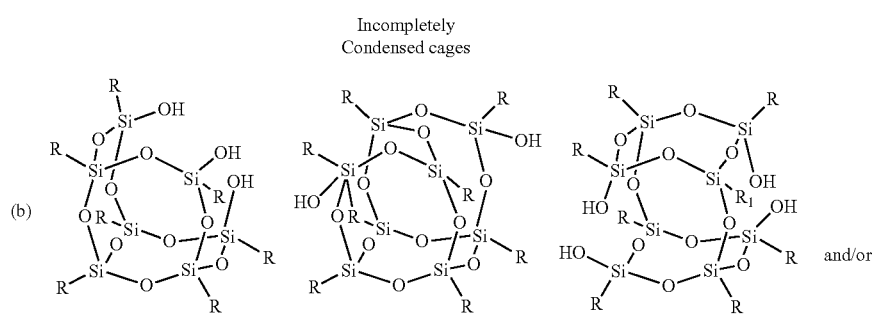

-continued
Non-cage content
Large & ill-defined structure

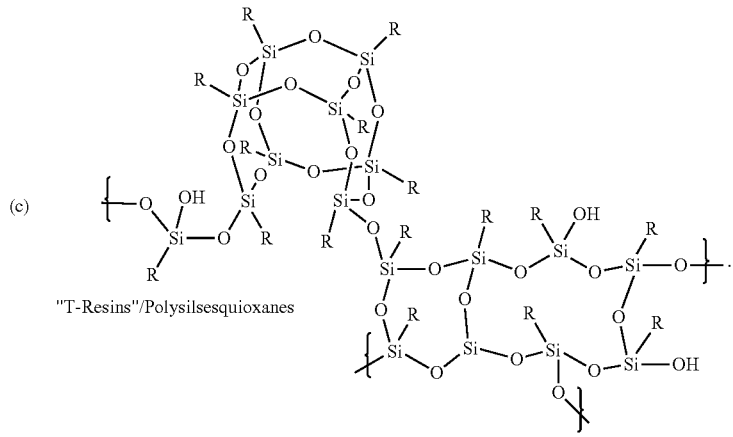

"T-Resins"/Polysilsesquioxanes

In the examples disclosed herein, at least one of $R_1$ through $R_8$ or $R_{10}$ or $R_{12}$ comprises an epoxy, and thus the POSS is referred to as an epoxy POSS. In some examples, a majority of the arms, such as the eight, ten, or twelve arms, or R groups, comprise epoxy groups. In other examples, $R_1$ through $R_8$ or $R_{10}$ or $R_{12}$ are the same, and thus each of $R_1$ through $R_8$ or $R_{10}$ or $R_{12}$ comprises an epoxy group. Throughout this disclosure, this type of POSS (i.e., in which $R_1$ through $R_8$ or $R_{10}$ or $R_{12}$ comprise the same epoxy group) may be represented by the word "POSS" with a particular epoxy functional group shown attached to the POSS. For example,

is the POSS cage with an epoxycyclohexylmethyl functional group as each of $R_1$ through $R_8$ or $R_{10}$ or $R_{12}$. In other examples, $R_1$ through $R_8$ or $R_{10}$ or $R_{12}$ are not the same, and thus at least one of $R_1$ through $R_8$ or $R_{10}$ or $R_{12}$ comprises epoxy and at least one other of $R_1$ through $R_8$ or $R_{10}$ or $R_{12}$ is a non-epoxy functional group, which in some cases is selected from the group consisting of an azide/azido, a thiol, a poly(ethylene glycol), a norbornene, and a tetrazine, or further, for example, alkyl, aryl, alkoxy, and haloalkyl groups. In some aspects, the non-epoxy functional group is selected to increase the surface energy of the resin. In these other examples, the ratio of epoxy groups to non-epoxy groups ranges from 7:1 to 1:7, or 9:1 to 1:9, or 11:1 to 1:11. In any of the examples, disubstituted or monosubstituted (terminal) epoxy group(s) allow the monomeric unit to polymerize into a cross-linked matrix (i.e., resin film) upon initiation using ultraviolet (UV) light and an acid. In some aspects, the epoxy POSS comprises terminal epoxy groups.

When the epoxy POSS is referred to as a "modified epoxy POSS," it is meant that a controlled radical polymerization (CRP) agent and/or another functional group of interest is incorporated into the resin or core or cage structure as one or more of the functional group $R_1$ through $R_8$ or $R_{10}$ or $R_{12}$. Similarly, when the epoxy POSS resin film is referred to as a "modified epoxy POSS resin film," it is meant that a controlled radical polymerization (CRP) agent and/or another functional group of interest is incorporated into the cross-linked matrix.

As used herein, the "primer" is defined as a single stranded nucleic acid sequence (e.g., single strand DNA or single strand RNA) that serves as a starting point for DNA or RNA synthesis. The 5' terminus of the primer may be modified to allow a coupling reaction with the coating layer of the functionalized molecule. The primer length can be any number of bases long and can include a variety of non-natural nucleotides. In an example, the sequencing primer is a short strand, including from 10 to 60 bases.

As used herein, the term "sensitizer" refers to a reagent that promotes photoreactivity of component monomers by release of a reactive species such as a free radical, e.g., a photoinitiator, a free radical initiator, azobisisobutyronitrile (AIBN), benzoyl peroxide, 1-hydroxycyclohexyl phenyl ketone (HCPK), or a thioxanthenone. In some aspects, the sensitizer is selected to provide improved energy matching with the photoacid generator such that acid is released from the photoacid generator under the selected uv conditions.

As used herein, the term "silane" refers to an organic or inorganic compound containing one or more silicon atoms. An example of an inorganic silane compound is $SiH_4$, or halogenated $SiH_4$ where hydrogen is replaced by one or more halogen atoms. An example of an organic silane compound is $X—R^B—Si(OR^C)_3$, wherein X is a functionalizable organic group, such as amino, methacrylate, thiol, alkyl, alkenyl, cycloalkenyl, alkynyl, or epoxy, which can be used to bond with a surface and/or a polymer; $R^B$ is a spacer, for example an alkylene, heteroalkylene, or $—(CH_2)_n—$, wherein n is 0 to 1000 or 1 to 100 or 1 to 10 or 2 to 6; $R^C$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. In some instances, each $R^C$ is the same, and in others, they may be different. In some examples, X is alkenyl or cycloalkenyl, $R^B$ is $—(CH_2)_n—$, wherein n is 2 to 6, and/or $R^C$ is alkyl. In another example, a silane compound is X—$R^B$—Si($R^D$)$_3$, where X and $R^B$ are as defined above, and each $R^D$ is independently $R^C$ or $OR^C$. In some examples, X comprises a substrate or support. Generally, the alkoxysilane moiety is used to condense with —OH groups such as on the surface of a metal oxide or plasma-treated epoxy POSS network. The X functional group is orthogonal to the alkoxysilane, and is used to separately couple with a CRP or other initiator. The orthogonal nature of the reactive groups allows for incorporation of the CRP unit after the POSS resin curing step, or after a silanization step of the cross-linked resin. As used herein, the term "silane" can include mixtures of different silane and/or silane derivative compounds.

The terms "substrate" and "support" are used interchangeably herein, and refer to a material on which a resin film is deposited. Examples of suitable supports include glass and modified or functionalized glass, plastics (including acrylics, polystyrene and copolymers of styrene and other materials, poly(vinyl chloride), polyesters, polycarbonates, poly(methyl methacrylate), polypropylene, polyethylene, polybutylene, polyurethanes, polytetrafluoroethylene (PTFE) (such as TEFLON® from Chemours), cyclic olefins/cyclo-olefin polymers (COP) or copolymers (COC) (such as ZEONOR® from Zeon), polyimides, etc.), nylon, ceramics, silica, fused silica, or other silica-based materials, silicon and modified silicon, silicon dioxide, silicon nitride, silicon hydride, carbon, metals, inorganic glasses, and optical fiber bundles. While several examples have been provided, it is to be understood that any other suitable substrate/support may be used.

The term "surface chemistry," as used herein refers to a polymer coating or polymer brush and primer(s) attached to at least a portion of an epoxy POSS resin film on a surface of a support/substrate.

A "thiol" functional group refers to —SH (e.g.,

As used herein, the terms "tetrazine" and "tetrazinyl" refer to six-membered heteroaryl group including four nitrogen atoms. Tetrazine can be optionally substituted. In an example, tetrazine is part of multi-ring structure where the rings do not share carbon atoms (e.g.,

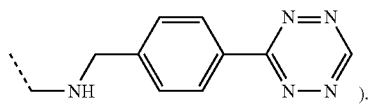

"Tetrazole," as used herein, refer to five-membered heterocyclic group including four nitrogen atoms.

The term "wetting agent," as used herein, refers to an additive that aids in surface coverage by components of the resin precursor mixture. Examples include surfactants, such as polyacrylate surfactants or silicone surfactants.

As used herein, the term "YES method" refers a chemical vapor deposition process developed by Illumina, Inc. which uses the chemical vapor deposition tool provided by Yield Engineering Systems ("YES"). The tool includes three different vapor deposition systems. The automated YES-VertaCoat silane vapor system is designed for volume production with a flexible wafer handling module that can accommodate 200 mm or 300 mm wafers. The manual load YES-1224P Silane Vapor System is designed for versatile volume production with its configurable large capacity chambers. Yes-LabKote is a low-cost, tabletop version that is ideal for feasibility studies and for R&D.

The aspects and examples set forth herein and recited in the claims can be understood in view of the above definitions.

FIGS. 1A through 1F together illustrate an example of the method disclosed herein, which forms an example of the array disclosed herein. FIG. 1E is an enlarged view of a depression of the array that is formed.

FIG. 1A illustrates a support 12 with a cross-linked epoxy POSS resin film 14 formed thereon. Any example of the support 12 previously described herein may be used. In an example, the support 12 with the cross-linked epoxy POSS resin film 14 formed thereon is commercially available. In another example, the cross-linked epoxy POSS resin film 14 is formed on the support 12.

Generally, the cross-linked epoxy POSS resin film 14 may be formed by forming a resin precursor, depositing the resin precursor on a surface of the support 12, and irradiating UV light to cure the resin precursor and to form the cross-linked epoxy POSS resin film 14.

The resin precursor is a mixture, which includes at least an epoxy POSS monomeric unit. The precursor comprises silicon-containing moieties such as D-silicons (attached to two oxygens), T-silicons (attached to 3 oxygens), and Q-silicons (attached to 4 oxygens). As discussed above, the POSS materials may comprise cage polyhedral structures, discrete but incompletely condensed polyhedral structures, or non-discrete silsesquioxane structures, each of varying size. Examples of the epoxy POSS monomeric units include epoxycyclohexyl alkyl POSS (where the alkyl is a linker between the POSS cage and the epoxycyclohexyl groups, and is methyl, ethyl, etc.), glycidyl POSS (where the $R_1$-$R_8$ or $R_{10}$ or $R_{12}$ groups include an alkyl (e.g., methyl, ethyl, propyl, etc.) attached to a glycidyl ether; e.g.,

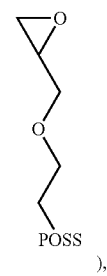

octaglycidyldimethylsilyl POSS, or the like. In some examples, the resin precursor includes one type of epoxy POSS monomeric unit. In other examples, the resin precursor includes different epoxy POSS monomeric units. When two different epoxy POSS monomeric units are used in combination, any suitable mass or molar ratio of the two units may be selected. For example, a first epoxy POSS monomeric unit may be present in an amount (X) ranging from about 10 mol % to about 90 mol % of the total amount of epoxy POSS monomeric units and a second epoxy POSS monomeric unit may make up the balance of the total monomeric units (i.e., 100 mol %-X mol %). In an example, the epoxycyclohexylalkyl POSS and glycidyl POSS are used together in a mass or molar ratio of about 3:1, although, as previously noted, other mass or molar ratios may be used.

In some examples, the resin precursor also includes an epoxy silane or another reactive silane that can be incorporated into the cross-linked POSS resin matrix. The epoxy silane includes an epoxy group at one end of the molecule and a silane at the other end of the molecule. The epoxy group can be incorporated covalently into the epoxy POSS resin film (by reaction of the epoxy group) and the silane group can covalently attach to surface groups (e.g., —OH) of the support 12. The epoxy silane may be included when the support 12 does not include surface-activating agent(s) that can adhere the epoxy POSS resin film to the support 12. However, it is to be understood that epoxy silane may be excluded when the support 12 is a silica-based substrate with a suitable surface-activating agent that can adhere the epoxy POSS resin film to the support 12.

In other examples when the support 12 does not include surface-activating agent(s), the resin precursor used to form the cross-linked epoxy POSS resin film 14 may not include the epoxy silane or other reactive silane. Rather, the epoxy silane or other reactive silane and at least one of the epoxy POSS monomeric unit(s) may be deposited first to attach the silane to the support 12, and then the previously described resin precursor (without the silane) may be reacted with the silane to form the cross-linked epoxy POSS resin film 14.

The resin precursor may also include a photoacid generator (PAG), a sensitizer, a solvent, and/or a wetting agent. These components may be added in any suitable amount to aid in polymerization and/or in deposition of the resin precursor. In some aspects of all of the methods described herein, the resin precursor comprises a wetting agent, such as a polyacrylate surfactant or a silicone surfactant.

In some examples, incompletely condensed silsesquioxane materials in the POSS precursor (which contain silanol groups) react with the substrate surface to bind the resin to the surface.

Scheme 1 illustrates one example of the resin precursor and the cross-linked epoxy POSS resin film formed therefrom.

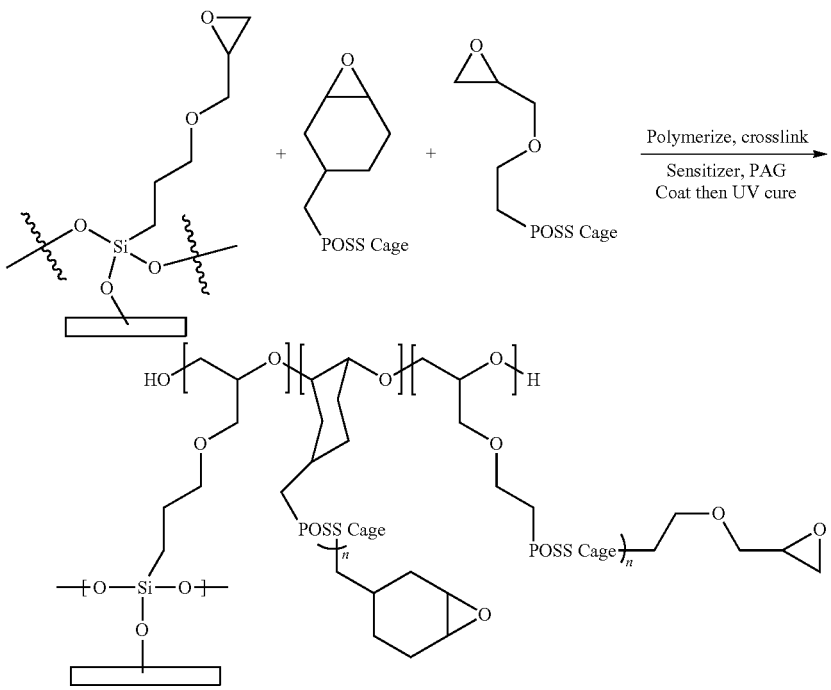

Scheme 1A depicts another example of the cross-linked resin film.

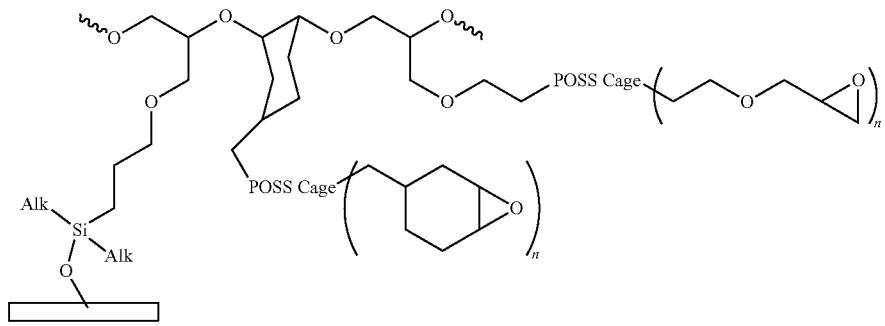

One of ordinary skill will understand that the polymers shown are exemplary, as individual monomers may combine in any order or polymeric pattern, and additional monomers may be attached to the monomeric units shown, e.g., the pendant arms of the cages may be linked to further monomers.

As depicted, in this example, the resin precursor is formed by mixing the epoxy silane (which can attach to the support 12 via an oxygen linkage as illustrated in Scheme 1), epoxycyclohexylalkyl POSS, and glycidyl POSS in the presence of a sensitizer and PAG. The support-bound epoxy silane may in another example be of the structure Support-O—Si(R)$_2$—O—C$_{2-6}$alkykepoxide), where each R is an alkyl group such as a methyl or ethyl group. The resin precursor is formed in certain examples by mixing the support-bound epoxy resin with one or two different epoxy POSS monomeric units. In other examples, the resin precursor is deposited on the surface of the support 12 using any suitable deposition method. Curing (i.e., polymerization and cross-linking) of the resin precursor is performed by exposure to actinic radiation (such as ultraviolet (UV) radiation). This process results in the cross-linked epoxy POSS resin film 14. The ratio of monomers within the final cross-linked epoxy POSS resin film 14 depends upon the stoichiometry of the monomers in the initial resin precursor mixture.

In some examples of the method shown in FIGS. 1A through 1F, the cross-linked epoxy POSS resin film 14 may be exposed to a hard bake after curing. The hard bake helps to drive the cross-linking reaction to completion (e.g., UV initiates the polymerization/cross-linking process and the reaction continues in the dark until complete). The hard bake also incubates or dehydrates the cross-linked epoxy POSS resin film 14 to drive out any solvent(s) that may remain after curing. The duration of the hard bake may last from about 5 seconds to about 10 minutes at a temperature ranging from about 100° C. to about 300° C. An example of a device that can be used for hard baking includes a hot plate.

As illustrated in FIG. 1A, in some examples, the cross-linked epoxy POSS resin film 14 is not imprinted.

Figure 1B:
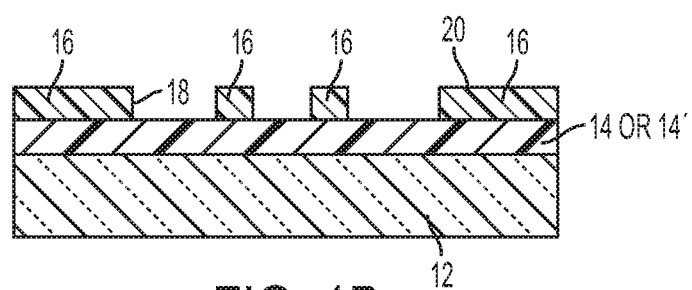

As shown between FIGS. 1A and 1B, two different Routes A or B may be performed. In Route A, the patterned hydrophobic polymer layer 16 is formed on the cross-linked epoxy POSS resin film 14 without further processing of the cross-linked epoxy POSS resin film 14. In Route B, the patterned hydrophobic polymer layer 16 is formed on the cross-linked epoxy POSS resin film 14 after additional processing is performed to introduce functional groups to the cross-linked epoxy POSS resin film 14 that can covalently bond to a functional group of a subsequently applied polymer coating 22.

With Route A, the cross-linked epoxy POSS resin film 14 is not exposed to additional processing before the patterned hydrophobic polymer layer 16 is formed. As such, the patterned hydrophobic polymer layer 16 is formed on the as-formed cross-linked epoxy POSS resin film 14.

The patterned hydrophobic polymer layer 16 may be made up of any polymer that is more hydrophobic than the cross-linked epoxy POSS resin film 14 and that does not adhere to the subsequently deposited polymer coating 22. Examples of the hydrophobic polymer include a fluorinated polymer, a negative tone photoresist, or a polysiloxane. The fluorinated polymer may be an amorphous (non-crystalline) fluoropolymer (e.g., CYTOP® from Bellex), a crystalline fluoropolymer, or a fluoropolymer having both amorphous and crystalline domains. Any suitable negative tone photoresist may be used, such as epoxy-based negative photoresists (e.g., the SU-8 series from MicroChem). Any suitable polysiloxane may also be used, such as polydimethylsiloxane (PDMS).

The patterned hydrophobic polymer layer 16 may be formed via any suitable technique. In one example to form the patterned hydrophobic polymer layer 16, the hydrophobic polymer is deposited (e.g., spin coated, etc.) on the cross-linked epoxy POSS resin film 14 and the deposited hydrophobic polymer is patterned using nanoimprint lithography and/or photolithography. In another example to form the patterned hydrophobic polymer layer 16, the hydrophobic polymer is deposited in the desired pattern on the cross-linked epoxy POSS resin film 14 using inkjet printing and/or microcontact printing.

The patterned hydrophobic polymer layer 16 may be a continuous layer which includes interstitial regions 20 separating adjacent depressions 18. At each depression 18, discrete areas of the cross-linked epoxy POSS resin film 14 are exposed (as shown in FIG. 1B).

Many different layouts of the depressions 18 may be envisaged, including regular, repeating, and non-regular patterns. In an example, the depressions 18 are disposed in a hexagonal grid for close packing and improved density. Other layouts may include, for example, rectilinear (i.e., rectangular) layouts, triangular layouts, and so forth. The layout or pattern can be an x-y format of depressions 18 that are in rows and columns. In some other examples, the layout or pattern can be a repeating arrangement of depressions 18 and/or interstitial regions 20. In still other examples, the layout or pattern can be a random arrangement of depressions 18 and/or interstitial regions 20. The pattern may include spots, pads, wells, posts, stripes, swirls, lines, triangles, rectangles (e.g., defining flow channels), circles, arcs, checks, plaids, diagonals, arrows, squares, and/or cross-hatches. In some examples, the pattern includes wells. Still other examples of patterned surfaces that can be used in the examples set forth herein are described in U.S. Pat. Nos. 8,778,849; 9,079,148; 8,778,848; and U.S. Patent Publication No. 2014/0243224, each of which is incorporated herein by reference in its entirety.

The layout or pattern may be characterized with respect to the density of the depressions 18 (i.e., number of depressions 18) in a defined area. For example, the depressions 18 may be present at a density of approximately 2 million per mm$^2$. The density may be tuned to different densities including, for example, a density of at least about 100 per mm$^2$, about 1,000 per mm$^2$, about 0.1 million per mm$^2$, about 1 million per mm$^2$, about 2 million per mm$^2$, about 5 million per mm$^2$, about 10 million per mm$^2$, about 50 million per mm$^2$, or more. Alternatively or additionally, the density may be tuned to be no more than about 50 million per mm$^2$, about 10 million per mm$^2$, about 5 million per mm$^2$, about 2 million per mm$^2$, about 1 million per mm$^2$, about 0.1 million per mm$^2$, about 1,000 per mm$^2$, about 100 per mm$^2$, or less. It is to be further understood that the density of depressions 18 defined by the patterned hydrophobic polymer layer 16 can be between one of the lower values and one of the upper values selected from the ranges above. As examples, a high density array may be characterized as having depressions 18 separated by less than about 1 μm of interstitial region 20, and a low density array may be characterized as having depressions 18 separated by greater than about 1 μm of interstitial region 20.

The layout or pattern may also or alternatively be characterized in terms of the average pitch, i.e., the spacing from the center of the depressions 18 to the center of an adjacent interstitial region 20 (center-to-center spacing). The pattern can be regular such that the coefficient of variation around the average pitch is small, or the pattern can be non-regular in which case the coefficient of variation can be relatively large. In either case, the average pitch can be, for example, at least about 10 nm, about 0.1 μm, about 0.5 μm, about 1 μm, about 5 μm, about 10 μm, about 100 μm, or more. Alternatively or additionally, the average pitch can be, for example, at most about 100 μm, about 10 μm, about 5 μm, about 1 μm, about 0.5 μm, about 0.1 μm, or less. The average pitch for a particular pattern of depressions 18 can be between one of the lower values and one of the upper values selected from the ranges above. In an example, the depressions 18 have a pitch (center-to-center spacing) of about 1.5 μm.

In the example shown in FIG. 1B, the depressions 18 are wells. The wells may be micro wells or nanowells. Each well may be characterized by its volume, well opening area, depth, and/or diameter.

Each well can have any volume that is capable of confining a liquid. The minimum or maximum volume can be selected, for example, to accommodate the throughput (e.g. multiplexity), resolution, analyte composition, or analyte reactivity expected for downstream uses of the array 10' (shown in FIG. 1F). For example, the volume can be at least about $1 \times 10^{-3}$ μm$^3$, about $1 \times 10^{-2}$ μm$^3$, about 0.1 μm$^3$, about 1 μm$^3$, about 10 μm$^3$, about 100 μm$^3$, or more. Alternatively or additionally, the volume can be at most about $1 \times 10^4$ μm$^3$, about $1 \times 10^3$ μm$^3$, about 100 μm$^3$, about 10 μm$^3$, about 1 μm$^3$, about 0.1 μm$^3$, or less.

The area occupied by each well opening on a surface can be selected based upon similar criteria as those set forth above for well volume. For example, the area for each well opening on a surface can be at least about $1 \times 10^{-3}$ μm$^2$, about $1 \times 10^{-2}$ μm$^2$, about 0.1 μm$^2$, about 1 μm$^2$, about 10 μm$^2$, about 100 μm$^2$, or more. Alternatively or additionally, the area can be at most about $1 \times 10^3$ μm$^2$, about 100 μm$^2$, about 10 μm$^2$, about 1 μm$^2$, about 0.1 μm$^2$, about $1 \times 10^{-2}$ μm$^2$, or less.

The depth of each well can be at least about 0.1 μm, about 1 μm, about 10 μm, about 100 μm, or more. Alternatively or additionally, the depth can be at most about $1 \times 10^3$ μm, about 100 μm, about 10 about 1 μm, about 0.1 μm, or less.

In some instances, the diameter of each well can be at least about 50 nm, about 0.1 μm, about 0.5 μm, about 1 μm, about 10 μm, about 100 μm, or more. Alternatively or additionally, the diameter can be at most about $1 \times 10^3$ μm, about 100 μm, about 10 μm, about 1 μm, about 0.5 μm, about 0.1 μm, or less (e.g., about 50 nm).

With Route B shown between FIGS. 1A and 1B, the cross-linked epoxy POSS resin film 14 is exposed to additional processing before the patterned hydrophobic polymer layer 16 is formed thereon in the manner previously described.

This additional processing may include plasma ashing or a chemical treatment to introduce hydroxyl groups to the cross-linked epoxy POSS resin film 14. In some examples, the processing is oxygen plasma ashing, and the process introduces free —OH groups (e.g., hydroxyl and/or carboxyl groups) to the resin film. Scheme 2 illustrates one example of the introduction of hydroxyl groups to the cross-linked epoxy POSS resin film 14.

Scheme 2: Plasma Ashing of Cross-linked Epoxy POSS Resin Film

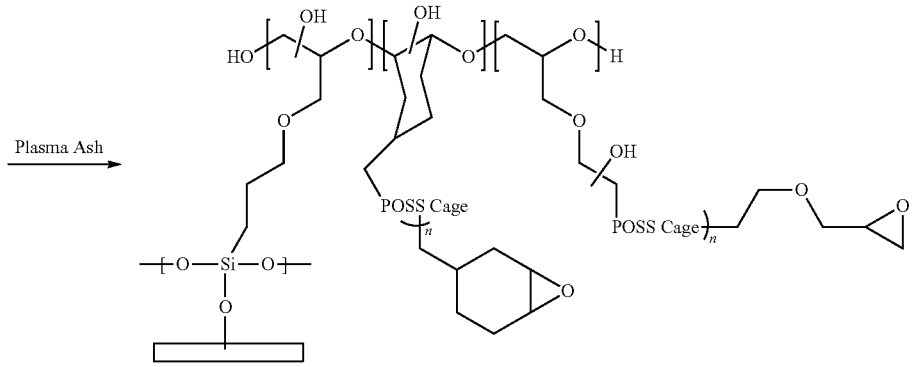

Scheme 2A illustrates another example of the introduction of hydroxyl groups to the cross-linked epoxy POSS resin film 14.

Scheme 2A: Plasma Ashing of Cross-linked Epoxy POSS Resin Film

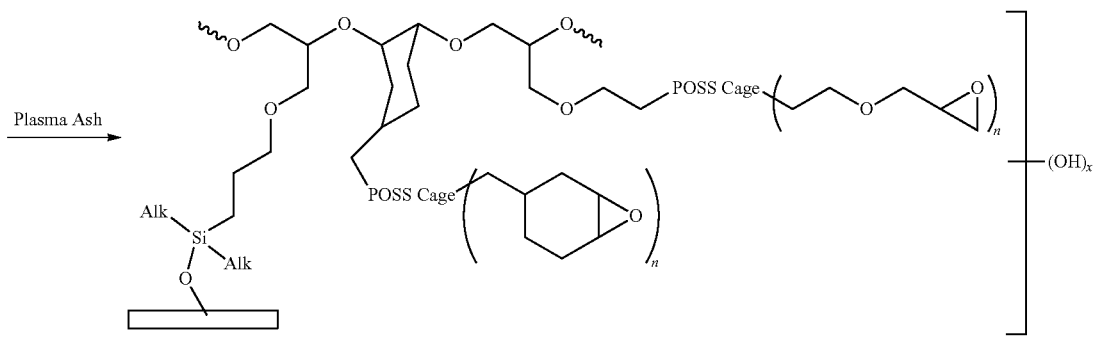

The hydroxyl group containing cross-linked epoxy POSS resin film 14 may then exposed to silanization or another chemical process to introduce functional groups (e.g., "FG" in FIG. 1E) that can attach to the hydroxyl group(s). These functional groups FG may be anchor molecules that enhance the attachment of the subsequently applied polymer coating 22 to the cross-linked epoxy POSS resin film 14 exposed in the depressions 18. As such, the selection of the functional group FG may depend, in part, upon the molecule that is to be used to form the polymer coating 22 (shown in FIG. 1C), as it may be desirable to form a covalent bond and/or a non-covalent bond (e.g., van der Waals or Hydrogen) between the functional group FG and the subsequently deposited polymer coating 22. Examples of the functional groups FG are selected from the group consisting of:

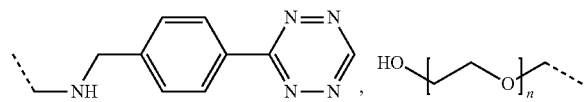

wherein n ranges from 1 to 20,

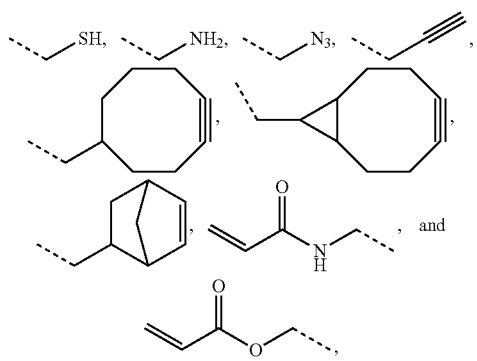

and wherein - - - represents an alkylsilane (e.g., by reaction of the hydroxyl groups with a trialkoxyalkylsilane), a poly (ethylene glycol)-silane (e.g., by reaction of the hydroxyl groups with a trialkoxysilane poly(ethylene glycol)), or an alkyl halide-silane (e.g., by reaction of the hydroxyl groups with an alkyl halide), or a polyethylene glycol chain, or any other silane that can form a tripodal connection with the hydroxyl group(s), or another group that can form a C—C—O— connection at the hydroxyl group(s). These functional groups, or any other functional groups that can withstand the processing that is performed during the formation of the patterned hydrophobic coating layer 16, may be used. The process conditions may also be adjusted to utilize a desirable functional group. While several examples of functional groups have been provided, it is to be understood that other hydrophilic or hydrophobic functional groups that can be covalently bonded to, or entrapped by the epoxy POSS resin film 14, and that introduces a desirable functionality to the epoxy POSS resin film 14 may be used. Still further, derivatives of the various functional groups FG and/or substituted variations of the functional groups FG may be used. In other examples, the polymer coating can be coated and cured to the cross-linked epoxy POSS resin film directly after plasma ashing, without a separate silanization or functionalization step.

The method used to attach the functional group FG to the hydroxyl groups of the cross-linked epoxy POSS resin film 14 may vary depending upon the functional group FG that is being used. Examples of suitable methods include vapor deposition, the YES method, solution deposition methods, or other deposition methods.

With Route B, the cross-linked epoxy POSS resin film 14 is modified to form a functionalized cross-linked epoxy POSS resin film 14'. The patterned hydrophobic polymer layer 16 (including its interstitial regions 20 and depressions 18) may then be formed in the manner previously described on the functionalized cross-linked epoxy POSS resin film 14'. In this example, discrete portions of the functionalized cross-linked epoxy POSS resin film 14' are exposed at the depressions 18.

Whether Route A or Route B is performed, after the patterned hydrophobic polymer layer 16 is formed, the polymer coating 22 is applied or grown on the patterned hydrophobic polymer layer 16 and in the depressions 18. This is shown in FIG. 1C.

The polymer coating 22 may be deposited on the patterned hydrophobic polymer layer 16 and on the exposed surfaces of the cross-linked epoxy POSS resin film 14 or the functionalized cross-linked epoxy POSS resin film 14' using spin coating, dipping or dip coating, spray coating, or the like. In an example, the polymer coating 22 is deposited as a solution, an example of which includes PAZAM in an ethanol and water mixture. Any solvent or solvent combination may be used that aids in wetting. Surfactants may also be added to the solution to aid in wetting.

After being coated, the polymer coating 22 may be exposed to a curing process to form attached coating portion(s) 22' (where the polymer coating 22 attaches to the exposed cross-linked epoxy POSS resin film 14 or functionalized cross-linked epoxy POSS resin film 14' in the depressions 18) and unattached coating portion(s) 22" (where polymer coating 22 does not attach to the patterned hydrophobic polymer layer 16 (e.g., at the interstitial regions 20)). The curing temperature may range from about 20° C. to about 80° C. and the curing time may range from seconds to about 120 minutes. In an example, curing the polymer coating 22 may take place at about 60° C. for about 1 hour. Curing temperature and time may vary depending, in part, on the polymer coating 22 being formed.

When Route B is utilized to form the functionalized cross-linked epoxy POSS resin film 14', the polymer coating 22 may be grown from the surface of the resin film 14'. For example, the support 12 having the resin film 14' and the patterned hydrophobic polymer layer 16 may be immersed into a suitable bath containing monomer(s) and an initiator. Polymerization of the monomer(s) will form the attached portion(s) 22' of the polymer coating 22.

The attached and unattached coating portion(s) 22', 22" are shown in FIG. 1C. The mechanism for attachment of the attached coating portion(s) 22' will depend upon whether the cross-linked epoxy POSS resin film 14 is present (Route A) or whether the functionalized cross-linked epoxy POSS resin film 14' is present (Route B).

As an example, the polymer coating 22 can attach to, or be inserted into unreacted epoxy groups of the cross-linked epoxy POSS resin film 14 to form the attached coating portion(s) 22'. For example, free amines on the polymer structure (e.g., Formula (I)) may react with unreacted epoxy groups in the cross-linked epoxy POSS resin film 14.

As another example, the polymer coating 22 can attach to the added functional group(s) FG of the functionalized cross-linked epoxy POSS resin film 14' to form the attached coating portion(s) 22'. The reaction that takes place will depend upon the functional group FG of the functionalized cross-linked epoxy POSS resin film 14' and the functional group of the polymer coating 22. The following are some examples of the reactions that can take place.

When the functional group FG of the functionalized cross-linked epoxy POSS resin film 14' is norbornene or a norbornene derivative, the norbornene or a norbornene derivative can: i) undergo a 1,3-dipolar cycloaddition reaction (i.e., click reaction) with an azide/azido group of PAZAM or a Formula (I) polymer; ii) undergo a coupling reaction with a tetrazine group attached to the polymer structure (e.g., Formula (I)); iii) undergo a cycloaddition reaction with a hydrazone group attached to the polymer structure (e.g., Formula (I)); iv) undergo a photo-click reaction with a tetrazole group attached to the polymer structure (e.g., Formula (I)); or v) undergo a cycloaddition with a nitrile oxide group attached to the polymer structure (e.g., Formula (I)). An example of the norbornene or a norbornene functional group undergoing the 1,3-dipolar cycloaddition reaction with the azide/azido group of PAZAM is shown in Scheme 3.

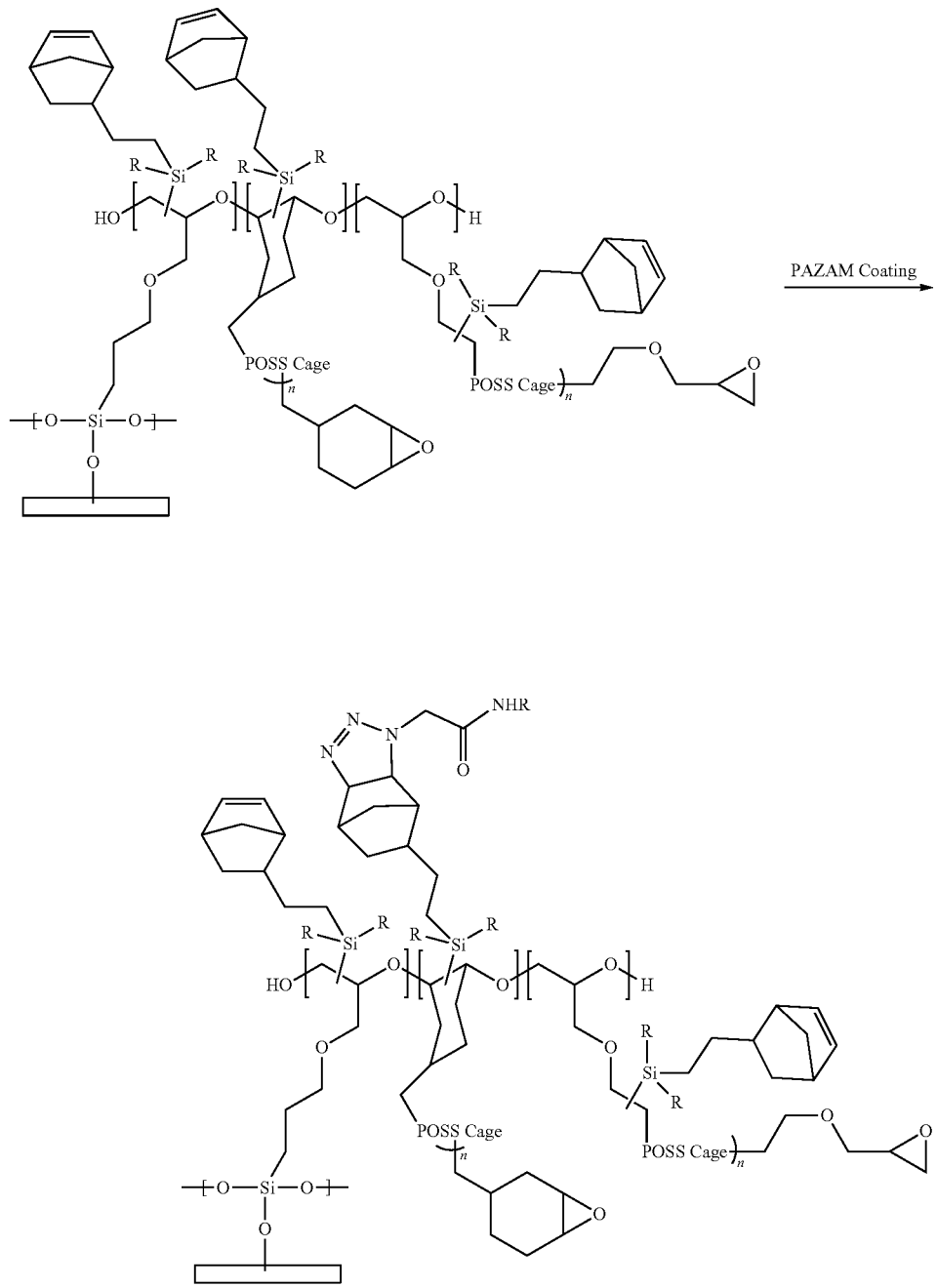

Scheme 3: Click Reaction between FG of Resin Film 14' and Polymer Coating 22 where the —CH$_2$C(O)NHR group is the side chain of the PAZAM polymer.

In other examples, the functional group FG of the functionalized cross-linked epoxy POSS resin is introduced at the hydroxyl positions that were added by the surface functionalization methods described above. An example is shown in Scheme 3A, where FG is a functional group as described herein.

When the functional group FG of the functionalized cross-linked epoxy POSS resin film 14' is cyclooctyne or a cyclooctyne derivative, the cyclooctyne or cyclooctyne derivative can: i) undergo a strain-promoted azide-alkyne 1,3-cycloaddition (SPAAC) reaction with an azide/azido of PAZAM (or other polymer such as a Formula (I) polymer), Scheme 3A: Introduction of Functional Groups

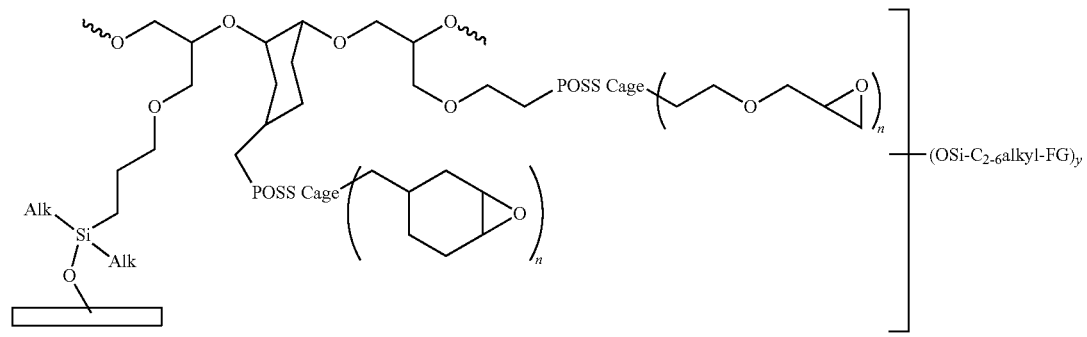

In some examples, the added functional groups comprise alkene or cycloalkane groups. In an example, such groups are shown in Scheme 3B.

or ii) undergo a strain-promoted alkyne-nitrile oxide cycloaddition reaction with a nitrile oxide group attached to a polymer (such as Formula (I)).

Scheme 3B: Introduction of Alkenyl or Cycloalkenyl Functional Groups

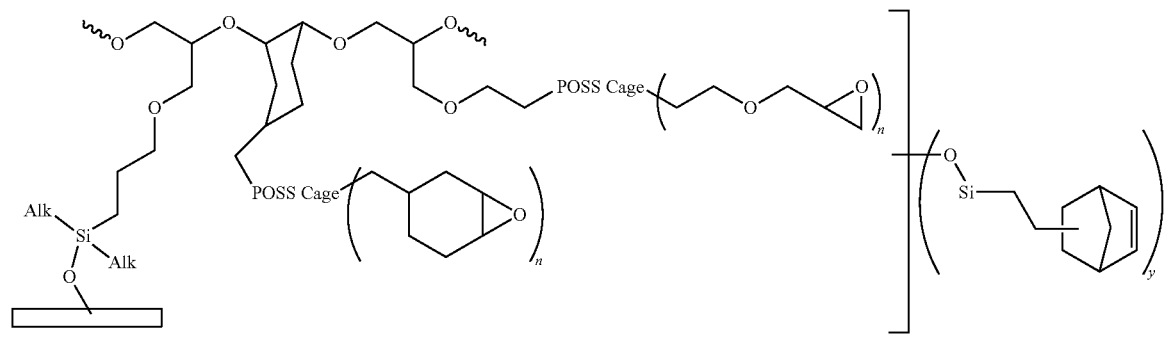

In an example, introduction of the polymer coating 22 is accomplished by reaction of the polymer material, such as a polymer of Formula (I), or PAZAM, or a combination of SFA and azido- or bromo-functionalized SFA, with the appended functional groups. An example is shown in Scheme 3C, showing just one reaction site on the POSS resin film. One of ordinary skill will recognize that reaction of the polymer coating with the functionalized POSS resin film occurs at multiple locations of the polymer and resin.

Scheme 3C: Addition of Polymer Coating

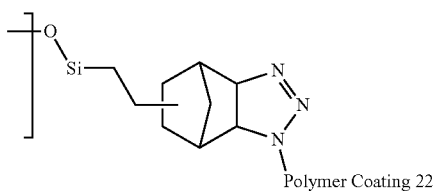

When the functional group FG of the functionalized cross-linked epoxy POSS resin film 14' is a bicyclononyne, the bicyclononyne can undergo similar SPAAC alkyne cycloaddition with azides or nitrile oxides attached to PAZAM (or other suitable polymer material such as a Formula (I) polymer) due to the strain in the bicyclic ring system.

After the attached and unattached coating portion(s) 22', 22" are formed, the unattached coating portion(s) 22" may be washed off of the patterned hydrophobic layer 16 (and in some instances off of the attached coating portion(s) 22'). The washing process may utilize a water bath and sonication. The water bath may be maintained at a relatively low temperature ranging from about 20° C. to about 60° C. FIG. 1D shows the array 10 after the unattached coating portion(s) 22" is/are removed.

FIG. 1E is an enlarged view of one of the depressions 18 after the attached coating portion 22' has been formed therein. In the example shown in FIG. 1E, the functionalized cross-linked epoxy POSS resin film 14' is formed and norbornene silane is the functional group FG that is added to the surface of the cross-linked epoxy POSS resin film 14'. The PAZAM attaches to the functional group FG to form the attached coating portion 22' within the depression 18 defined by the patterned hydrophobic polymer layer 16.

Referring now to FIG. 1F, an amplification primer 24 may be grafted to the attached polymer coating portion 22'. Examples of suitable primers 24 include forward amplification primers or reverse amplification primers. Specific examples of suitable primers 24 include P5 or P7 primers, which are used on the surface of commercial flow cells sold by Illumina Inc. for sequencing on HiSeq®, HiSeqX®, MiSeq®, NextSeq® and Genome Analyzer® instrument platforms.

The amplification primer 24 may be modified at the 5' end with a group that is capable of reacting with a functional group of the attached coating portion 22' (e.g., the azide shown in FIG. 1E). For example, a bicyclo[6.1.0] non-4-yne (BCN) terminated primer may be captured by an azide of the attached coating portion 22' via strain-promoted catalyst free click chemistry. For another example, an alkyne terminated primer may be captured by an azide of the attached coating portion 22' via copper catalyzed click chemistry. For still another example, a norbornene terminated primer, may be undergo a catalyst-free ring strain promoted click reaction with a tetrazine functionalized attached coating portion 22'. Other examples of terminated primers that may be used include a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, and a triazolinedione terminated primer. Other examples of terminated primers are thiophosphate-terminated primers.

Grafting may be accomplished by dunk coating, spray coating, puddle dispensing, or by another suitable method that will attach the primer(s) 24 to attached coating portions 22' in at least some of the depressions 18. Each of these examples may utilize a primer solution or mixture, which may include the primer(s) 24, water, a buffer, and an optional catalyst(s).

Dunk coating may involve submerging (via an automated or manual process) the array 10 (shown in FIG. 1D) into a series of temperature controlled baths. The baths may include the primer solution or mixture. Throughout the various baths, the primer(s) 24 will attach to the attached coating portions 22' in at least some of the depression(s) 18. In an example, the array 10 will be introduced into a first bath including the primer solution or mixture where a reaction takes place to attach the primer(s) 24, and then the array 10' will be moved to additional baths for washing.

Spray coating may be accomplished by spraying the primer solution or mixture directly onto the array 10. The spray coated array may be incubated for a time ranging from about 5 minutes to about 60 minutes at a temperature ranging from about 10° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the array 10. The applied primer solution or mixture may be applied to or spread across the entire surface of the array 10. The primer coated array 10 may be incubated for a time ranging from about 5 minutes to about 60 minutes at a temperature ranging from about 10° C. to about 80° C. After incubation, the primer solution or mixture may be diluted and removed using, for example, the spin coater.

After grafting, the desired surface chemistry has been applied, and the array 10' may be used in a variety of sequencing approaches or technologies.

The example of the method shown in FIGS. 1A-1F may also be performed with modified epoxy POSS monomeric unit. In this example, the resin precursor includes the epoxy POSS monomeric unit(s) previously described and a modified epoxy POSS monomeric unit. In these examples, at least one of $R_1$ through $R_8$ or $R_{10}$ or $R_{12}$ of the modified epoxy POSS monomeric unit is an epoxy group (for incorporation into the epoxy POSS resin film 14) and at least one of $R_1$ through $R_8$ or $R_{10}$ or $R_{12}$ is another functional group that can covalently or non-covalently bond to a functional group of a subsequently applied polymer coating 22. As such, in this example, the other functional group is incorporated directly into the POSS core or cage structure. Examples of the other functional group include any of the examples of the functional group FG.

Resin precursors including the modified epoxy POSS monomeric unit(s) may include from about 50 mol % to about 90 mol % of the epoxy POSS monomeric unit(s) and from about 10 mol % to about 50 mol % of the modified epoxy POSS monomeric unit(s) (i.e., 100 mol %-X mol % of the epoxy POSS monomeric unit(s)). As such, the mass or molar ratio of epoxy POSS monomeric unit(s) to modified epoxy POSS monomeric unit(s) in some examples of the resin precursors ranges from about 1:1 to about 9:1. In these resin precursors, when two different (non-modified) epoxy POSS monomeric units are used in combination, any suitable mass or molar ratio of the two units may be selected. For example, a first epoxy POSS monomeric unit (e.g., epoxycyclohexylalkyl POSS) may be present in an amount (Y) ranging from about 10 mol % to about 90 mol % of the total amount of epoxy POSS monomeric units and a second epoxy POSS monomeric unit (e.g., glycidyl POSS) may make up the balance of the total epoxy POSS monomeric units (i.e., 100 mol % of epoxy POSS monomeric units-Y mol %). In other examples, any of the epoxy POSS monomeric units and any of the modified epoxy POSS monomeric units may be present in an amount ranging from about 10 mol % to about 90 mol %.

The use of the modified epoxy POSS monomeric unit to form the resin film introduces the functional group FG directly into the backbone of the resin film, and thus provides a site (other than the unreacted epoxy groups) for attachment of the polymeric coating 22 without having to perform further processes on the resin film as described in Route B.

FIGS. 2A through 2D together illustrate another example of the method disclosed herein, which forms another example of the array disclosed herein. FIG. 2C is an enlarged view of a depression of the array that is formed.

In the example method(s) shown in FIGS. 2A through 2D, a modified epoxy POSS resin film 14" is formed, which includes a controlled radical polymerization (CRP) agent (shown schematically as 26 in FIG. 2C) incorporated into the cross-linked matrix. The CRP agent 26 may be a reversible addition-fragmentation chain transfer (RAFT) agent or an atom transfer radical polymerization (ATRP) initiator. For the RAFT agents, the orientation of the thiocarbonyl group at the surface affects the polymerization. In one example, the RAFT agent is capable of covalently attaching to the surface of the modified epoxy POSS resin film 14" via the stabilizing group such that the growing radical chain moves away from the surface. This is referred to as the Z-group approach. In another example, the RAFT attaches to the surface via a leaving and initiating group (i.e., the R-group approach). The R-group approach may afford greater control over the molecular weight, and chain-chain coupling may be minimized.

As will be described further herein, the CRP agent 26 may be incorporated into the cross-linked matrix during curing or after curing, and may be incorporated into the backbone of the cross-linked matrix (via a non-POSS monomeric unit or a modified epoxy POSS monomeric unit) or may be attached to the backbone via another functional group.

FIG. 2A illustrates a support 12 with the modified epoxy POSS resin film 14" formed thereon. Any example of the support 12 previously described herein may be used. In an example, the modified epoxy POSS resin film 14" is formed on the support 12, and FIG. 2A illustrates three routes, shown as Route C, Route D, and Route E, for forming the modified epoxy POSS resin film 14".

Using Route C, a resin precursor is formed which includes a CRP-containing monomeric unit, the resin precursor is deposited on a surface of the support 12, and the resin precursor is irradiated with UV light to cure and form the cross-linked epoxy POSS resin film 14". As such, Route C involves incorporating the CRP agent 26 into the backbone of the cross-linked matrix of the resin film 14" during curing of the resin precursor.

In this example, the resin precursor is a mixture, which includes at least an epoxy POSS monomeric unit and a CRP-containing monomeric unit. Any examples of the epoxy POSS monomeric units described herein may be used. The CRP-containing monomeric unit may be a non-POSS monomeric unit or a modified epoxy POSS monomeric unit.

The CRP-containing non-POSS monomeric unit does not include a POSS core. Rather, the CRP agent 26 is tethered to a functional group that can be incorporated covalently into the modified epoxy POSS resin film 14" with the epoxy POSS monomeric unit(s). As an example, the CRP agent 26 may be reacted with an epoxy functional group to form an epoxy-functionalized CRP agent, such as an epoxy-functionalized RAFT agent (Scheme 4) or an epoxy-functionalized ATRP initiator (Scheme 5).

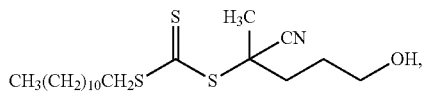

which can be reacted with any epoxyhalohydrin (e.g., epichlorohydrin

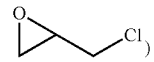

)

to form another example of the epoxy-functionalized RAFT agent.

Scheme 5: Formation of an Epoxy-Functionalized ATRP Initiator

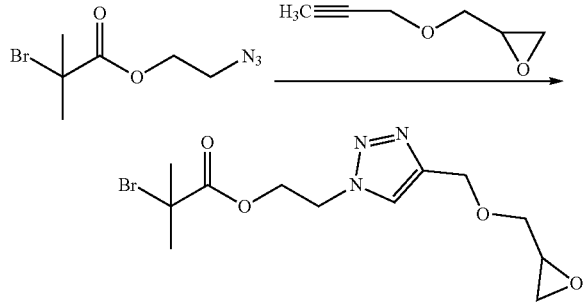

In Scheme 5, the ATRP initiator is 2-azidoethyl 2-bromoisobutyrate and the epoxy functional group is glycidyl propargyl ether. It is to be understood that other commercially available ATRP initiators or other prepared ATRP initiators may be used, such as Poly(ethylene glycol) methyl ether 2-bromoisobutyrate.

As mentioned above, the CRP-containing monomeric unit may be a modified epoxy POSS monomeric unit. In these Scheme 4: Formation of an Epoxy-Functionalized RAFT Agent

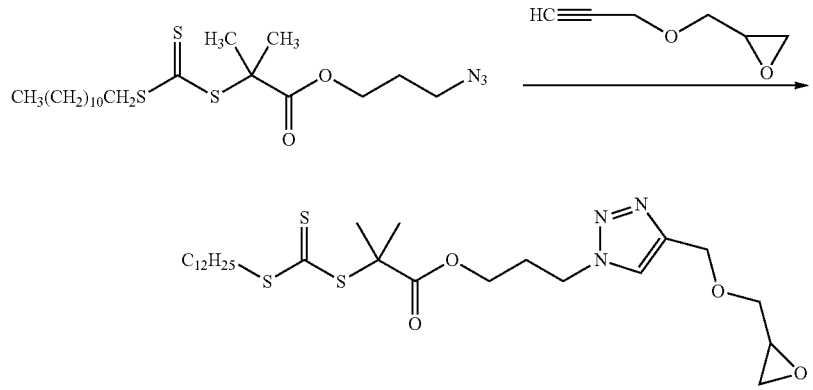

In Scheme 4, the RAFT agent is 2-(dodecylthiocarbonothioylthio)-2-methylpropionic acid 3-azido-1-propanol ester and the epoxy functional group is glycidyl propargyl ether. It is to be understood that other commercially available RAFT agents or other prepared RAFT agents may be used. Another suitable RAFT agent is 4-cyano-4-[(dodecylsulfanylthiocarbonyl)sulfanyl]pentanol:

examples, the monomeric unit is the POSS core having an epoxy group (for incorporation into the epoxy POSS resin film 14") as at least one of $R_1$ through $R_8$ or $R_{10}$ or $R_{12}$ and having the CRP agent 26 as at least one of $R_1$ through $R_8$ or $R_{10}$ or $R_{12}$. As such, in this example, the CRP agent 26 is incorporated directly into the POSS core or cage structure. As examples, any RAFT agent with the structure

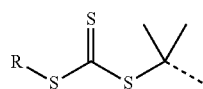

and any ATRP initiator with the structure

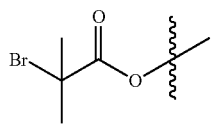

may be used, e.g., 2-azidoethyl 2-bromoisobutyrate, 2-bromoisobutyric anhydride, bromoisobutyryl bromide, or poly(ethylene glycol) bis(2-bromoisobutyrate). For example, the RAFT agent may be:

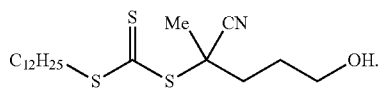

Other suitable RAFT agents are dithiobenzoates, trithiocarbonates, and dithiocarbamates. The specific RAFT agents or ATRP initiators previously mentioned may also be used to modify the epoxy POSS core/cage.

In Route C, the resin precursor including the CRP-containing monomeric unit(s) may include from about 50 mol % to about 90 mol % of the epoxy POSS monomeric unit(s) and from about 10 mol % to about 50 mol % of the CRP-containing monomeric unit(s) (i.e., 100 mol %-X mol % of the epoxy POSS monomeric unit(s)). As such, the molar or mass ratio of epoxy POSS monomeric unit(s) to CRP-containing monomeric unit(s) in some examples of the resin precursors ranges from about 1:1 to about 9:1. As one example, the molar or mass ratio of total epoxy POSS monomeric units (e.g., epoxycyclohexylalkyl POSS and glycidyl POSS) to epoxy-functionalized CRP agent(s) ranges from about 1:1 to about 9:1. In these resin precursors, when two different (non-modified) epoxy POSS monomeric units are used in combination, any suitable mass or molar ratio of the two units may be selected. For example, a first epoxy POSS monomeric unit (e.g., epoxycyclohexylalkyl POSS) may be present in an amount (Y) ranging from about 10 mol % to about 90 mol % of the total amount of epoxy POSS monomeric units and a second epoxy POSS monomeric unit (e.g., glycidyl POSS) may make up the balance of the total epoxy POSS monomeric units (i.e., 100 mol % of epoxy POSS monomeric units-Y mol %). In other examples, any of the epoxy POSS monomeric units and any of the CRP-containing monomeric unit(s) may be present in an amount ranging from about 10 mol % to about 90 mol %.

In some examples using Route C, the resin precursor also includes an epoxy silane or another reactive silane that can be incorporated into the cross-linked POSS resin matrix. The epoxy silane includes an epoxy group at one end of the molecule and a silane at the other end of the molecule. The epoxy group can be incorporated covalently into the modified epoxy POSS resin film 14" and the silane group can covalently attach to surface groups (e.g., —OH) of the support 12. The epoxy silane may be included when the support 12 does not include surface-activating agent(s) that can adhere the epoxy POSS resin film 14" to the support 12. However, it is to be understood that epoxy silane may be excluded when the support 12 is a silica-based substrate with a suitable surface-activating agent that can adhere the epoxy POSS resin film 14" to the support 12.

In other examples when the support 12 does not include surface-activating agent(s), the resin precursor used to form the modified cross-linked epoxy POSS resin film 14" may not include the epoxy silane or other reactive silane. Rather, the epoxy silane or other reactive silane and at least one of the epoxy POSS monomeric unit(s) may be deposited first to attach the silane to the support 12, and then the previously described resin precursor for Route C (without the silane) may be reacted with the silane to form the modified epoxy POSS resin film 14".

The resin precursor used in Route C may also include a photoacid generator (PAG), a sensitizer, a solvent, and/or a wetting agent. These components may be added in any suitable amount to aid in polymerization and/or in deposition of the resin precursor.

Schemes 6 and 7 illustrate examples of the resin precursors used in Route C and the modified epoxy POSS resin film formed therefrom. These examples illustrate the use of CRP-containing non-POSS monomeric unit.

Scheme 6: Polymerization of Modified Epoxy POSS Resin Film Using an Epoxy-Functionalized RAFT Agent

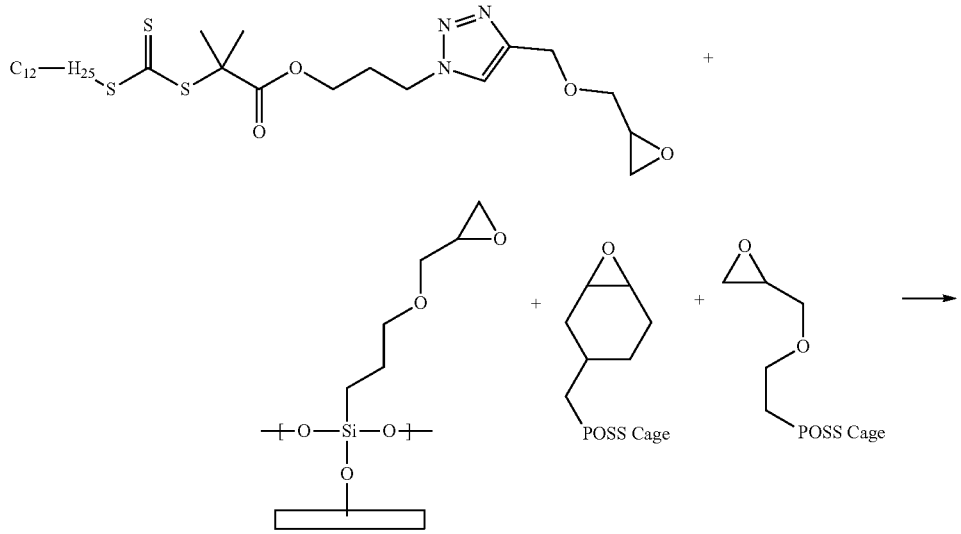

-continued
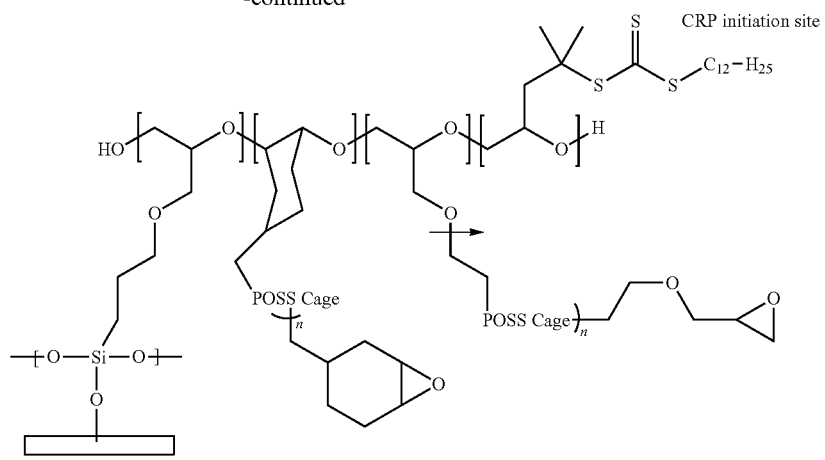
20
Scheme 7: Polymerization of Modified Epoxy POSS Resin Film Using an Epoxy-Functionalized ATRP Initiator
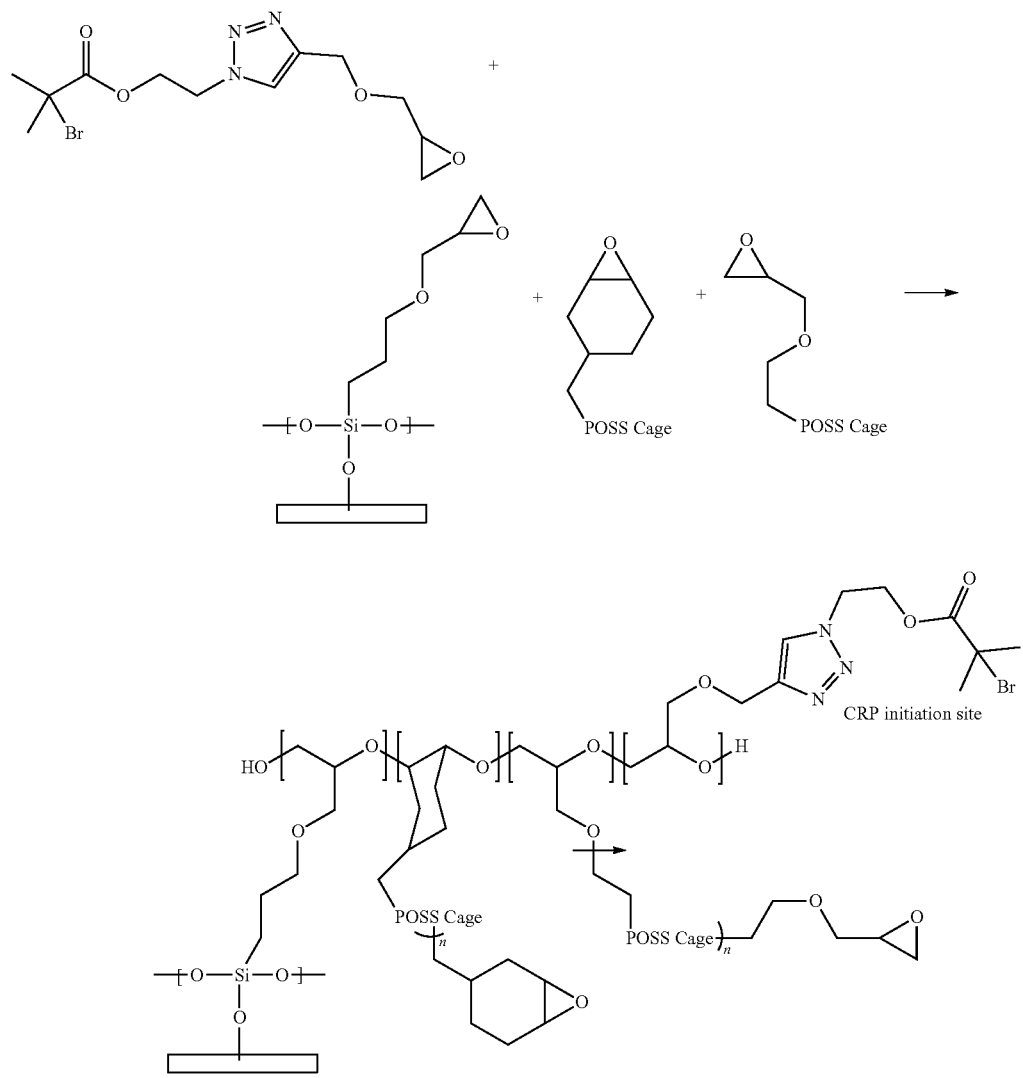

One of ordinary skill will recognize the POSS resin films depicted in Schemes 6 and 7 may also be depicted as shown in the preceding Schemes, and that the resin films are composed of monomeric units in any order or polymeric pattern (e.g., random, block, alternating, or combinations thereof).

In these examples, the resin precursor is formed by mixing the CRP-containing non-POSS monomeric unit (i.e., the epoxy-functionalized RAFT agent or the epoxy-functionalized ATRP initiator), epoxy silane or other reactive silane (which can attach to the support 12 via an oxygen linkage as illustrated in Schemes 6 and 7), epoxycyclohexylalkyl POSS, and glycidyl POSS in the presence of a sensitizer and PAG. The resin precursor is deposited on the surface of the support 12 using any suitable deposition method. Curing (i.e., polymerization and cross-linking) of the resin precursor is performed by exposure to actinic radiation (such as ultraviolet (UV) radiation). This process results in the cross-linked epoxy POSS resin films 14". The ratio of monomers within the final cross-linked epoxy POSS resin film 14" depends upon the stoichiometry of the monomers in the initial resin precursor mixture.

As illustrated in both Schemes 6 and 7, the CRP-containing non-POSS monomeric unit introduces a polymer growth initiation site (i.e., CRP initiation site) into the backbone of the cross-linked matrix of the resin film 14" during curing of the resin precursor. While not shown, it is to be understood that when the CRP-containing epoxy POSS monomeric unit is used instead of the CRP-containing non-POSS monomeric unit, the backbone of the cross-linked matrix will include an additional POSS cage to which the polymer growth initiation site (i.e., CRP initiation site) is attached.

Route D involves attaching the CRP agent 26 to the backbone of the cross-linked matrix via another functional group after the resin film 14" has been cured.

In this example, the resin precursor is a mixture similar to that described in reference to FIG. 1A. For example, the resin precursor in Route D may include the epoxy POSS monomeric unit(s), the epoxy silane or other reactive silane (e.g., when attachment to the support 12 is desirable), the photoacid generator (PAG), the sensitizer, the solvent, and/or the wetting agent. The resin precursor is deposited on the surface of the support 12 using any suitable deposition method. Curing (i.e., polymerization and cross-linking) of the resin precursor is performed by exposure to actinic radiation (such as ultraviolet (UV) radiation). This process results in a cross-linked epoxy POSS resin film, similar to resin film 14 previously described (see, e.g., Scheme 1). A hard bake may be performed as previously described. In Route D, it is to be understood that the epoxy silane or other reactive silane and at least one of the epoxy POSS monomeric unit(s) may be deposited first to attach the silane to the support 12, and then the previously described resin precursor for Route D (without the silane) may be reacted with the silane to form the cross-linked epoxy POSS resin film 14.

The cross-linked epoxy POSS resin film is then exposed to plasma ashing or a chemical treatment to introduce —OH groups (e.g., hydroxyl (C—OH or Si—OH) and/or carboxyl groups) to the cross-linked epoxy POSS resin film (e.g., as shown in Scheme 2).

The hydroxyl group containing cross-linked epoxy POSS resin film may then be exposed to silanization or another chemical process to introduce a functional group at the hydroxyl group, where the selected functional group can attach to a desired CRP agent 26. As such, the selection of the functional group in Route D may depend, in part, upon the CRP agent 26 that is to be attached. For example, a RAFT agent with a terminal azide group can react with an alkyne functional group that has been attached at the hydroxyl group of the cross-linked epoxy POSS resin film.

Examples of suitable functional groups for Route D are selected from the group consisting of

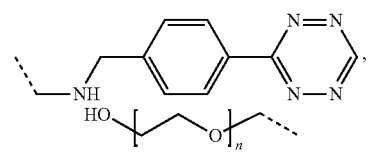

wherein n ranges from 1 to 20,

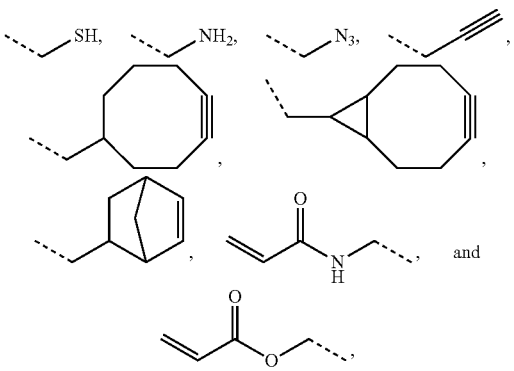

and wherein - - - represents a species that is capable of reacting with the —OH group of the cross-linked epoxy POSS resin film. Examples of - - - include an alkylsilane (e.g., by reaction of the hydroxyl groups with a trialkoxyalkylsilane), a poly(ethylene glycol)-silane (e.g., by reaction of the hydroxyl groups with a trialkoxysilane poly(ethylene glycol)), or an alkyl halide-silane (e.g., by reaction of the hydroxyl groups with an alkyl halide), or a polyethylene glycol chain, or any other silane that can form a tripodal connection with the hydroxyl group(s), or another group that can form a C—C—O— connection at the hydroxyl group(s). Some specific examples include of the functional groups include silane PEG azide (Polysciences, Inc.), silane PEG alkyne (Polysciences, Inc.), 3-azidopropyltriethoxysilane (Gelest), or (Bicyclo[2.2.1]hept-5-en-2-yl)triethoxysilane. While several examples have been provided, it is to be understood that any functional group that can attach to the hydroxyl group(s) of the cross-linked epoxy POSS resin film and to the CRP agent 26 may be used.

The method used to attach the functional group to the hydroxyl groups of the cross-linked epoxy POSS resin film may vary depending upon the functional group that is being used. Examples of suitable methods include vapor deposition, the YES method, solution deposition methods (e.g., dunk coating), or other deposition methods.

Any of the CRP agents 26 previously described (e.g., 2-(dodecylthiocarbonothioylthio)-2-methylpropionic acid 3-azido-1-propanol ester, 4-cyano-4-[(dodecylsulfanylthiocarbonyl)sulfanyl]pentanol, etc.) may then be attached to the functional group of the cross-linked epoxy POSS resin film. The method used to attach the CRP agents 26 to the functional group of the cross-linked epoxy POSS resin film may vary depending upon the CRP agent 26 that is being used. Examples of suitable methods include solution deposition methods.

With Route D, the cross-linked epoxy POSS resin film is first modified to add the previously described functional group(s), and then the CRP agent 26 is attached to at least some of the functional groups to form an example of the modified epoxy POSS resin film 14" (which includes a polymer growth initiation site).

Like Route D, Route E involves attaching the CRP agent 26 to the backbone of the cross-linked matrix after the resin film 14" has been cured.

In Route E, the resin precursor is a mixture including the epoxy POSS monomeric unit(s) and a modified epoxy POSS monomeric unit. In this example of the modified epoxy POSS monomeric unit, at least one of $R_1$ through $R_8$ or $R_{10}$ or $R_{12}$ is an epoxy group (for incorporation into the epoxy POSS resin film 14") and at least one of $R_1$ through $R_8$ or $R_{10}$ or $R_{12}$ is a non-epoxy functional group that can attach to the CRP agent 26 (e.g., the non-epoxy functional group may be selected from the group consisting of an azide, a thiol, a poly(ethylene glycol), a norbornene, and a tetrazine). This non-epoxy functional group will be integrated into an initially modified epoxy POSS resin film during curing.

Resin precursors for Route E may include from about 50 mol % to about 90 mol % of the epoxy POSS monomeric unit(s) and from about 10 mol % to about 50 mol % of the modified epoxy POSS monomeric unit(s) (i.e., 100 mol %-X mol % of the epoxy POSS monomeric unit(s)). As such, the molar or mass ratio of epoxy POSS monomeric unit(s) to modified epoxy POSS monomeric unit(s) in some examples of the resin precursors ranges from about 1:1 to about 9:1. In these resin precursors, when two different (non-modified) epoxy POSS monomeric units are used in combination, any suitable mass or molar ratio of the two units may be selected. For example, a first epoxy POSS monomeric unit (e.g., epoxycyclohexylalkyl POSS) may be present in an amount (Y) ranging from about 10 mol % to about 90 mol % of the total amount of epoxy POSS monomeric units and a second epoxy POSS monomeric unit (e.g., glycidyl POSS) may make up the balance of the total epoxy POSS monomeric units (i.e., 100 mol % of epoxy POSS monomeric units-Y mol %). In other examples, any of the epoxy POSS monomeric units and any of the modified monomeric unit(s) may be present in an amount ranging from about 10 mol % to about 90 mol %.

The resin precursor for Route E may also include the epoxy silane or other reactive silane (e.g., when attachment to the support 12 is desirable), the photoacid generator (PAG), the sensitizer, the solvent, and/or the wetting agent. The resin precursor is deposited on the surface of the support 12 using any suitable deposition method. Curing (i.e., polymerization and cross-linking) of the resin precursor is performed by exposure to actinic radiation (such as ultraviolet (UV) radiation). This process results in an initially modified epoxy POSS resin film, which includes the non-epoxy functional group. A hard bake may be performed as previously described. In Route E, it is to be understood that the epoxy silane or other reactive silane and at least one of the epoxy POSS monomeric unit(s) may be deposited first to attach the silane to the support 12, and then the previously described resin precursor for Route E (without the silane) may be reacted with the silane to form the cross-linked epoxy POSS resin film 14".

A desired CRP agent 26 may then be introduced to the initially modified epoxy POSS resin film to form the modified epoxy resin film 14" including the polymer growth initiation site. The CRP agent 26 may be attached to the non-epoxy functional group using any of the solution deposition techniques (e.g., dunk coating, etc.) previously described herein. The CRP agent 26 will be selected so that it can react with any of the non-epoxy functional groups disclosed herein (e.g., azide, thiol, poly(ethylene glycol), norbornene, or tetrazine functional groups).

Routes C, D, and E all result in the formation of the modified epoxy resin film 14" on the support 12. The modified epoxy resin film 14" includes the polymer growth initiation site because of the attached/integrated CRP agent 26. As illustrated in FIG. 2A, the modified epoxy POSS resin film 14" is not imprinted.

The patterned hydrophobic polymer layer 16 (including its interstitial regions 20 and depressions 18) may then be formed in the manner previously described on the modified epoxy POSS resin film 14". In this example, discrete portions of the modified epoxy POSS resin film 14" are exposed at the depressions 18. The formed patterned hydrophobic polymer layer 16 is shown in FIG. 2B.

The method of FIGS. 2A through 2D then involves growing the polymer brush 28 from the polymer growth initiation site/CRP agent 26. The grown polymer brush 28 is shown in FIG. 2C. Polymer growth may be performed in dunk tanks which include the support 12 having the layers 14" and 16 thereon and a suitable monomer that is to be polymerized. Examples of suitable monomers include acrylamides (e.g., a PAZAM monomer or another acrylamide that is capable of attaching the primer 24), or acrylates.

Scheme 8 illustrates an example of the polymer brush formation. This scheme shows both an acrylamide (left) and an acrylate (right) polymerized from an ATRP initiator/CRP agent 26 (i.e.,

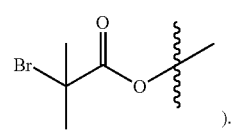

).

Scheme 8: Polymer Brush Growth from an ATRP Initiator/Polymer Growth Initiation Site

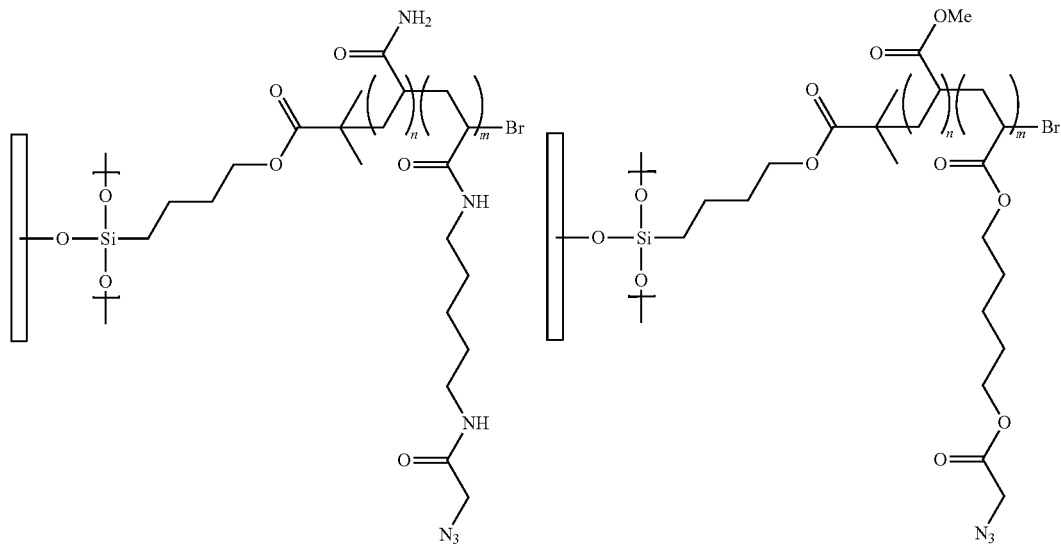

It is noted that the modified epoxy POSS resin film 14" is represented by the silane group and the - - - between the silane group and CRP agent 26. Polymer growth from acrylamide and acrylate monomers may also be accomplished when the modified epoxy POSS resin film 14" has a RAFT CRP agent 26 attached thereto.

The polymerization conditions may depend upon the monomer(s) and the CRP agent 26 of the modified epoxy POSS resin film 14". As an example, solution-state conditions may be used for polymer brush growth.

FIG. 2B shows the array 10" after the polymer brush 28 is formed in the depressions 18 (exposed discrete areas of the modified epoxy POSS resin film 14").

Referring now to FIG. 2D, an amplification primer 24 may be grafted to the polymer brush 28. Any suitable amplification primer 24 may be used, and the amplification primer 24 may be modified at the 5' end with a group that is capable of reacting with a functional group of the polymer brush 28. For example, a bicyclo[6.1.0] non-4-yne (BCN) terminated primer may be captured by an azide of the polymer brush 28 via strain-promoted catalyst free click chemistry. For another example, an alkyne terminated primer may be captured by an azide of the polymer brush 28 via copper catalyzed click chemistry. For still another example, a norbornene terminated primer, may be undergo a catalyst-free ring strain promoted click reaction with a tetrazine functionalized attached polymer brush 28. Other examples of terminated primers that may be used include a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, and a triazolinedione terminated primer. Other terminated primers include thiophosphate-terminated primers.

Grafting may be accomplished as previously described, e.g., by dunk coating, spray coating, puddle dispensing, or by another suitable method that will attach the primer(s) 24 to the polymer brush 28 in at least some of the depressions 18.

After grafting, the desired surface chemistry has been applied, and the array 10''' (FIG. 2D) may be used in a variety of sequencing approaches or technologies.

While several examples of the epoxy POSS resin film 14, 14', 14" have been disclosed herein, it is to be understood that layered epoxy POSS resin film 14, 14', 14" may be utilized, or that different epoxy POSS resin films 14, 14', 14" may be applied to/formed on different areas of the support 12. In the layered versions, different layers may be exposed at different areas in order to alter the functionality of the array at different locations.

The arrays 10', 10''' disclosed herein may be used in a variety of sequencing approaches or technologies, including techniques often referred to as sequencing-by-synthesis (SBS), sequencing-by-ligation, pyrosequencing, and so forth. With any of these techniques, since the attached coating portion 22' or polymer brush 28 and attached sequencing primers 24 are present in the depressions 18 and not on the interstitial regions 20, amplification will be confined to the various depressions 18.

Briefly, a sequencing by synthesis (SBS) reaction may be run on a system such as the HiSeq®, HiSeqX®, MiSeq® or NextSeq® sequencer systems from Illumina (San Diego, Calif.). A set of target DNA molecules to be sequenced is hybridized to the bound amplification primers 24 and then amplified, for example by kinetic exclusion amplification or by bridge amplification. Denaturation leaves single-stranded templates anchored to the attached coating portion 22' or polymer brush 28, and several million dense clusters of double-stranded DNA are generated (i.e., cluster generation). The sequencing reactions are carried out.

The arrays 10', 10' disclosed herein may also be disposed in or formed as a part of a flow cell, which is a chamber including a solid surface across which various carrier fluids, reagents, and so forth may be flowed. In an example, the flow cell may include the array 10', 10' bonded to a top substrate through a sealing material (e.g., black polyimide or another suitable bonding material). The bonding may take place in bonding regions of the patterned hydrophobic polymer layer 16, the sealing material, and the top substrate. The bonding regions may be located between flow channels so that the sealing material physically separates one flow channel from an adjacent flow channel (to prevent cross-contamination) and may be located at the periphery of the flow cell (to seal the flow cell from external contamination). It is to be understood, however, that the bonding regions and the sealing material may be located in any desired region depending on the implementation. Bonding may be accomplished via laser bonding, diffusion bonding, anodic bonding, eutectic bonding, plasma activation bonding, glass frit bonding, or others methods known in the art.

Other examples of flow cells and related fluidic systems and detection platforms that can be integrated with the array 10', 10" and/or readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference in its entirety.

In some applications, the flow cell is used to perform controlled chemical or biochemical reactions in a reaction automation device, such as in a nucleotide sequencer. Ports (not shown) may be drilled through the support 12, epoxy POSS resin film 14, 14', 14", and patterned hydrophobic polymer layer 16. Alternatively, the layers on the support 12 may be removed from those regions where it is desirable to form a port and/or bonding region. The layers may be removed prior to port drilling and bonding. By connecting to ports, the reaction automation device may control the flow of reagent(s) and product(s) in the sealed flow channels. The reaction automation device may, in some applications, adjust the pressure, temperature, gas composition and other environmental conditions of the flow cell. Further, in some applications, ports may be drilled in the top substrate or in both the top substrate and through the support 12, epoxy POSS resin film 14, 14', 14", and patterned hydrophobic polymer layer 16. In some applications, the reactions taking place in sealed flow channels may be monitored through the top substrate by imaging or measurements of heat, light emission and/or fluorescence.

Additional Notes

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All publications, patents, and patent applications cited in this Specification are hereby incorporated by reference in their entirety.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 10 kDa to about 1500 kDa, should be interpreted to include not only the explicitly recited limits of from about 10 kDa to about 1500 kDa, but also to include individual values, such as about 88 kDa, about 325 kDa, about 425 kDa, about 975.5 kDa, etc., and sub-ranges, such as from about 25 kDa to about 900 kDa, from about 335 kDa to about 680 KDa, etc. Furthermore, when "about" is utilized to describe a value, this is meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A method, comprising:
   forming a patterned hydrophobic polymer layer on a cross-linked epoxy polyhedral oligomeric silsesquioxane (POSS) resin film on a support surface, thereby exposing discrete areas of the cross-linked epoxy POSS resin film;
   applying a polymer coating to form an attached coating portion on the exposed discrete areas and an unattached coating portion on the patterned hydrophobic layer; and
   washing the unattached coating portion off of the patterned hydrophobic layer.

2. The method as defined in claim 1, further comprising forming the cross-linked epoxy POSS resin film on the support surface, the forming involving:
   mixing an epoxy silane and at least one epoxy POSS monomeric unit in the presence of a photoacid generator and optionally a sensitizer to form a resin precursor;
   depositing the resin precursor on the support surface; and
   curing the resin precursor to form the cross-linked epoxy POSS resin film.

3. The method as defined in claim 2, wherein the mixing and depositing occur at the same time.

4. The method as defined in claim 2, wherein the epoxy silane is an epoxy silane bound to the support surface.

5. The method as defined in claim 1, further comprising forming the cross-linked epoxy POSS resin film on the support surface, the forming involving:
   mixing an epoxy silane, epoxycyclohexylalkyl POSS, and glycidyl POSS in the presence of a photoacid generator and optionally a sensitizer to form a resin precursor;
   depositing the resin precursor on the support surface; and
   curing the resin precursor to form the cross-linked epoxy POSS resin film.

6. The method as defined in claim 1, wherein prior to forming the patterned hydrophobic polymer layer, the method further comprises:
   exposing the cross-linked epoxy POSS resin film to plasma ashing or a chemical treatment to introduce —OH groups to the cross-linked epoxy POSS resin film; and
   attaching functional groups to at least some of the —OH groups, the functional groups being selected from the group consisting of:

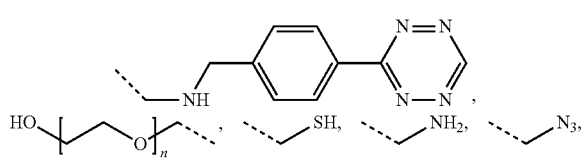

-continued

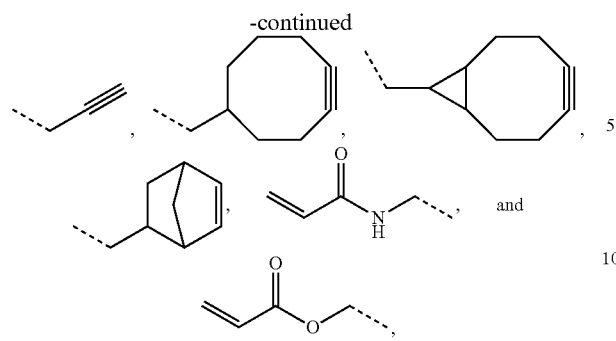

wherein n ranges from 1 to 20, and wherein - - - represents an alkylsilane, a poly(ethylene glycol)-silane, an alkyl, or a polyethylene glycol chain.

7. The method as defined in claim 1, further comprising forming the cross-linked epoxy POSS resin film on the support surface, the forming involving:

mixing, in the presence of a photoacid generator and optionally a sensitizer, an epoxy silane, epoxycyclohexylalkyl POSS, glycidyl POSS, and a POSS core including at least one epoxy functional group and a non-epoxy functional group to form a resin precursor;

depositing the resin precursor on the support surface; and curing the resin precursor to form the cross-linked epoxy POSS resin film.

8. The method as defined in claim 1, wherein washing involves sonication in water.

9. The method as defined in claim 1, wherein forming the patterned hydrophobic polymer layer involves:

i) depositing a hydrophobic polymer on the cross-linked epoxy POSS resin film; and patterning the deposited hydrophobic polymer using at least one of nanoimprint lithography and photolithography; or ii) depositing the hydrophobic polymer in a pattern on the cross-linked epoxy POSS resin film using at least one of inkjet printing and microcontact printing.

10. The method as defined in claim 1, further comprising grafting an amplification primer to the attached coating portion.

11. A method, comprising:

forming a cross-linked epoxy POSS resin film on a support surface, where the forming involves mixing a support-bound epoxy silane with one or more epoxy-functionalized POSS reagents in the presence of a photoacid generator and optionally a sensitizer to form a support-bound resin precursor;

curing the resin precursor to form a support-bound cross-linked epoxy POSS resin film; and forming a hydrophobic polymer layer on the cross-linked, support-bound epoxy POSS resin film, wherein the hydrophobic polymer layer is patterned to expose the cross-linked, support-bound epoxy POSS resin film in discrete areas or wells while remaining on the cross-linked, support-bound epoxy POSS resin film in interstitial areas of the cross-linked, support-bound epoxy POSS resin film between the discrete areas or wells.

12. The method as defined in claim 11, wherein the one or more epoxy-functionalized POSS reagents comprise an epoxycyclohexylalkyl POSS and a glycidyl POSS.

13. The method as defined in claim 11, further comprising reacting the support surface with an epoxy silane to form the support-bound epoxy silane.

* * * * *